(12) United States Patent
Qin et al.

(10) Patent No.: US 7,408,036 B2
(45) Date of Patent: Aug. 5, 2008

(54) HUMAN VOLTAGE GATED SODIUM CHANNEL β1A SUBUNIT AND METHODS OF USE

(75) Inventors: Ning Qin, Blue Bell, PA (US); Ellen Codd, Blue Bell, PA (US); Michael D'Andrea, Cherry Hill, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 11/370,490

(22) Filed: Mar. 8, 2006

(65) Prior Publication Data

US 2006/0269996 A1    Nov. 30, 2006

Related U.S. Application Data

(62) Division of application No. 10/401,916, filed on Mar. 28, 2003, now Pat. No. 7,063,953, which is a division of application No. 09/875,456, filed on Jun. 6, 2001, now Pat. No. 6,994,993.

(60) Provisional application No. 60/236,664, filed on Sep. 29, 2000, provisional application No. 60/294,405, filed on Jun. 7, 2000, now abandoned.

(51) Int. Cl.
*C07K 14/705*    (2006.01)

(52) U.S. Cl. ..................................................... 530/350

(58) Field of Classification Search ....................... None
See application file for complete search history.

*Primary Examiner*—John Ulm

(57) ABSTRACT

DNAs encoding human voltage gated sodium channel β1A subunit have been cloned and characterized. The recombinant protein is capable of forming biologically active protein. The cDNA's have been expressed in recombinant host cells that produce active recombinant protein. The recombinant protein is also purified from the recombinant host cells. In addition, the recombinant host cells are utilized to establish a method for identifying modulators of the receptor activity, and receptor modulators are identified.

2 Claims, 5 Drawing Sheets

```
hβ1A    1  MGRLLALVVGAALVSSACGGCVEVDSETEAVYGMTFKILCISCKRRSETN   50
           || ||||||||| ||||| ||||||||||||||||||||||||||||||
rβ1A    1  MGTLLALVVGAVLVSSAWGGCVEVDSETEAVYGMTFKILCISCKRRSETT   50 hβ1A   51  AETFTEWTFRQKGTEEFVKILRYENEVLQLEEDERFEGRVVWNGSRGTKD  100
           ||||||||||||||||||||||||||||||||||||||||||||||||||
rβ1A   51  AETFTEWTFRQKGTEEFVKILRYENEVLQLEEDERFEGRVVWNGSRGTKD  100 hβ1A  101  LQDLSIFITNVTYNHSGDYECHVYRLLFFENYEHNTSVVKKIHIEVVDKG  150
           |||||||||||||||||||||||||||||:|||||||||||||:||||||
rβ1A  101  LQDLSIFITNVTYNHSGDYECHVYRLLFFDNYEHNTSVVKKIHLEVVDKG  150 hβ1A  151  ESGAACPFTVTHRRARWRDRWQAVDRTGWLCAWPANRPQQRAEGEGSSPS  200
                  ||  ·|||||| ·  ||   | ·    · |·  ·|
rβ1A  151  KWS.....LVTLWQARWRDRWKEGDR...LVSHRGQLTPRSHRGK.DTPF  191 hβ1A  201  CPLQLWPLFLSSPRRGQ.SMPVPHRRSGYRTQLCHLCCMTSGRCL.LSLS  248
           |:   |  ·    ||   ||   ·|    | ||·||    |:  :|
rβ1A  192  LVLETSALQHTG...GQIRTPTPPPTNGMCIGL.HSCCVTSDGCIPISEP  237 hβ1A  249  QRVVLGLPGIIR..CVSRGVV.............  268
            |     |    |  |||·
rβ1A  238  QACPQGPERIFCMACCVSQAGPHWRDVGTYLRPQWE  273
```

B:

```
β1A     1  MGRLLALVVGAALVSSACGGCVEVDSETEAVYGMTFKILCISCKRRSETN   50
           ||||||||||||||||||||||||||||||||||||||||||||||||||
hβ1     1  MGRLLALVVGAALVSSACGGCVEVDSETEAVYGMTFKILCISCKRRSETN   50 hβ1A   51  AETFTEWTFRQKGTEEFVKILRYENEVLQLEEDERFEGRVVWNGSRGTKD  100
           ||||||||||||||||||||||||||||||||||||||||||||||||||
hβ1    51  AETFTEWTFRQKGTEEFVKILRYENEVLQLEEDERFEGRVVWNGSRGTKD  100 hβ1A  101  LQDLSIFITNVTYNHSGDYECHVYRLLFFENYEHNTSVVKKIHIEVVDKG  150
           ||||||||||||||||||||||||||||||||||||||||||||||||||
hβ1   101  LQDLSIFITNVTYNHSGDYECHVYRLLFFENYEHNTSVVKKIHIEVVDKA  150 hβ1A  151  ESGAACPFTVTHRRARWRDRWQAVDRTGWLCAWPANRPQQ.RAEGEGSSP  199
                |  ·:      :     |  |  ||  |    ·· |   |  ··
hβ1   151  NRDMA...SIVSEIMMY...VLIVVLTIWLVAEMIYCYKKIAAATETAAQ  194 hβ1A  200  SCPLQLWPLFLSSPRRGQSMPVPHRRSGYRTQLCHLCCMTSGRCLLSLSQ  249
            :   :     |    ·|
hβ1   195  ENASEYLAITSESKENCTGVQVAE.....................  218
```

A. L5, ipsilateral DRGs
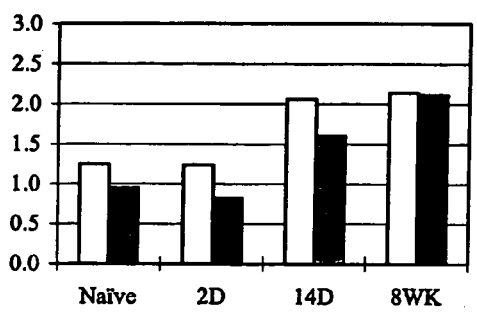
B. L5, contralateral DRGs
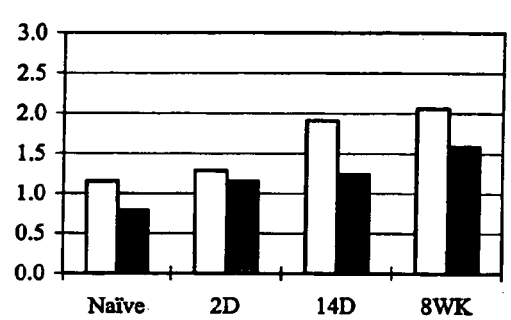
C. L4, ipsilateral DRGs
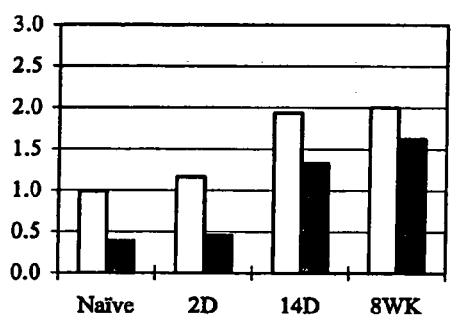
D. L4, contralateral DRGs
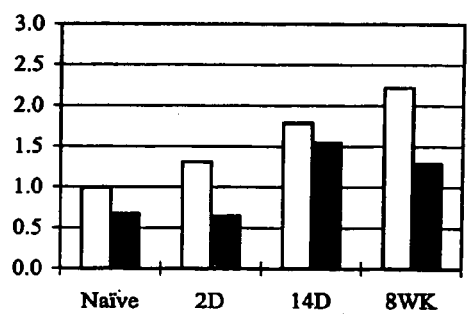
Figure 4

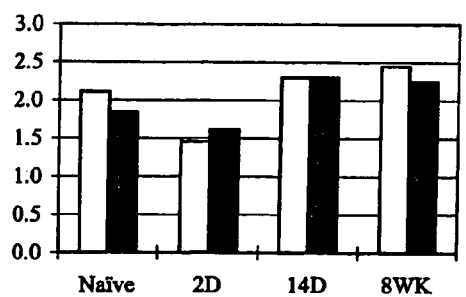
A. L5, ipsilateral DRGs
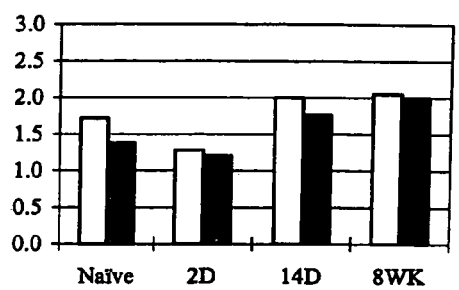
B. L5, contralateral DRGs
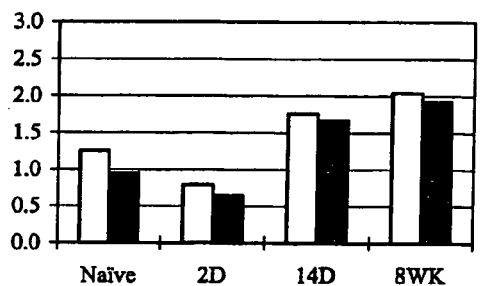
C. L4, ipsilateral DRGs
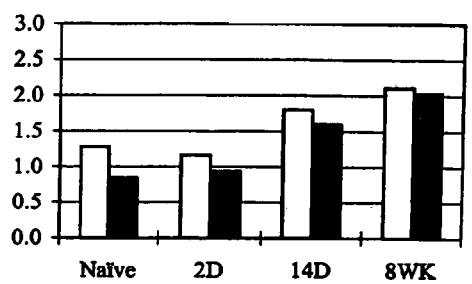
D. L4, contralateral DRGs
Figure 5

HUMAN VOLTAGE GATED SODIUM CHANNEL β1A SUBUNIT AND METHODS OF USE

This case is a divisional application of U.S. patent application Ser. No. 10/401,916 filed Mar. 28, 2003 now U.S. Pat. No. 7,063,953, which is a divisional application of U.S patent application Ser. No. 09/875,456 filed Jun. 6, 2001 now U.S. Pat. No. 6,994,993 and entitled "The Human Voltage Gated Sodium Channel β1A Subunit and Method of Use" which claims priority from U.S. Provisional Patent Application No. 60/294,405 filed Jun. 7, 2000 now abandoned and entitled "DNA Encoding Human Voltage Gated Sodium Channel β1A Subunit" and U.S Provisional Patent Application No. 60/236,664 filed Sep. 29, 2000 also entitled "DNA Encoding Human Voltage Gated Sodium Channel β1A Subunit" the contents of which are all hereby incorporated by reference in their entirety.

BACKGROUND OF THE INVENTION

Rapid entry of sodium ion into cells causes depolarization and generation of the action potential. Such entry of sodium ions in response to voltage change on the plasma membrane in excitable cells is mediated by voltage gated sodium channels (VGSC). Therefore, voltage gated sodium channels play a fundamental role in the control of neuronal excitability in the central and peripheral nervous systems. The VGSC is a protein complex comprising at least a large (200-300 kDa), pore forming, α subunit and two small (30-40 kD) regulatory β1 and β2 subunits (Catterall, 1992 & 1993; Isom et al., 1992; Isom et al., 1995). It is well known that VGSC α subunits determine the basic properties of the channel because expression of the α subunit of VGSC alone in the heterologous expression systems such as HEK cells, CHL cells and *Xenopus* oocytes is sufficient to synthesize a functional, but altered, sodium channel. Co-expression of VGSC β1 and β2 subunits with the α subunit will usually normalize the channel properties in heterologous expression systems. In order words, VGSC β1 and β2 subunits modulate almost all the aspects of the channel properties including voltage dependent gating, activation and inactivation, and increase the number of functional channels on the plasma membrane. The VGSC β subunits may also be the rate limiting step controlling the increased expression of sodium channels (Caterall, 1992; Isom et al., 1994)

Molecular cloning studies have demonstrated that there are many different types of VGSC α subunits, which can be categorized based on their sensitivity to neurotoxin and tetrodotoxin (TAX) (Marban, et al. 1998). Because brain VGSC type I, IIA, III, skeletal muscle type I, sodium channel protein 6 (SCP6), its closely homologous peripheral nerve 4 (PN4), and peripheral nerve 1 (PN1) are blocked by TTX at nanomolar concentrations, they are termed TTX-sensitive (TTX-S) sodium channels. The cardiac sodium channel (H1), and peripheral nerve 3 (PN3/SNS) and NaN/SNS2 are normally blocked by TTX in the micromolar range, and are termed TTX-resistant (TTX-R) sodium channels.

The studies of VGSC β subunits are far behind those of VGSC α subunits. So far, only two types of β subunits, β1 and β2 (Isom, et al. 1992, 1994 & 1995) have been cloned and characterized. Recently, a novel VGSC β1A subunit, a splicing variant of the β1 subunit, has been identified from rat (Kazen-Gillespie, et al. 2000). Rat VGSC β1A subunit results from an apparent intron retention event. Analysis of rat genomic DNA indicated the divergent region (carboxyl region) of β1A is encoded by intron 3 with an in-frame termination codon. Like the VGSC β1 subunit, the β1A subunit increases sodium current density and [$^3$H]Saxitoxin binding sites, and modulates voltage dependent activation and inactivation of the type IIA of VGSC. More interestingly, the expression level and pattern of the VGSC β1A in dorsal root ganglia (DRG) are changed significantly in the Chung animal neuropathic pain model (see below), which is consistent with the observation that the sodium current is increased after nerve injury. Both VGSC β1 and β1A subunits are integral membrane glycoproteins (Isom, et al. 1992, Kazen-Gillespie, et al. 2000) containing a single transmembrane domain at the carboxyl terminus and an extracellular amino-terminal immunoglobulin-like fold motif maintained by a single putative disulfide bridge between two highly conserved cysteine residues. VGSC β1 and β1A can be classified as members of the V-set of the Ig superfamily, which includes many cell adhesion molecule, suggesting that β1 and β1A subunits play roles not only in modulating sodium channel properties, but also in protein targeting and cell adhesion (Isom and Catteral, 1996).

An increase in the rate of spontaneous firing in neurons is often observed in peripheral sensory ganglia following nerve injury (Ochoa and Torebjork, 1980; Nordin et al., 1984; Devor, 1994; Woolf, 1994). It has been suggested that this hyperexcitability in neurons is due to altered sodium channel expression in some chronic pain syndromes (Tanaka et al., 1998). Increased numbers of sodium channels leading to inappropriate, repetitive firing of the neurons have been reported in the tips of injured axons in various peripheral nervous tissues such as the DRG which relay signals from the peripheral receptors into the central nervous system (Waxman and Brill, 1978; Devor et al., 1989; Matzner and Devor, 1992; Devor et al., 1992; England et al., 1994; Matzner and Devor, 1994; England et al., 1996). Transcripts encoding the α-III subunit, which are present at only very low levels in control DRG neurons, are expressed at moderate to high levels in axotomized DRG neurons together with elevated levels of α-I and α-II mRNAs (Waxman et al, 1994). Conversely, transcripts of sodium channel α-SNS are down-regulated in DRG neurons following axotomy (Dib-Hajj et al., 1996). Furthermore, the partial efficacy of sodium blocking agents is well documented in patients treated for neuropathic pain (Chabel et al., 1989; Devor et al., 1992; Omana-Zapata et al., 1997; Rizzo, 1997), providing an important link between increased sodium channel expression and neuropathic pain. Therefore, alterations in sodium channel expression and subsequent function may be a key molecular event underlying the pathophysiology of pain after peripheral nerve injury.

Recently the VGSC β1A subunit had been cloned and was reported to increase sodium current density at the plasma membrane when co-expressed with αIIA subunits in CHL fibroblasts (Kazan-Gillespie et al., 2000). β1A is developmentally regulated in the brain, but its potential role in neuropathic pain has not been previously explored. Therefore, the expression of β1A protein in DRG neurons using the Chung model of neuropathic pain (Kim and Chung, 1992) was investigated using a polyclonal antibody directed against a unique extracellular region of β1A not present in β1. Immunohistochemistry and computer-assisted image analysis documented significant up-regulation of VGSC β1A and β1 subunits following neuronal injury, compared to very low levels in the DRG from sham operated animal. The distinct punctate and membrane labeling distribution of β1A following peripheral nerve injury suggested active translation and possible accumulation into the plasma membrane, unlike β1, where the subcellular distribution remained diffuse.

To further explore the functions of VGSC β1A subunit, human VGSC β1A subunit has been cloned and characterized in this invention.

SUMMARY OF THE INVENTION

A DNA molecule encoding human VGSC β1A subunit has been cloned and characterized, and it represents a novel isoform of the human VGSC β1A subunit that is preferentially expressed in tissues important for neurological function. Using a recombinant expression system, functional DNA molecules encoding the channel subunit have been isolated. The biological and structural properties of these proteins are disclosed, as is the amino acid and nucleotide sequence. The recombinant DNA molecules and portions thereof, are useful for isolating homologues of the DNA molecules, identifying and isolating genomic equivalents of the DNA molecules, and identifying, detecting or isolating mutant forms of the DNA molecules.

Further, the β1A subunit is implicated in neuropathic pain as evidenced using an established neuropathic pain model.

In a first aspect of the invention, the invention relates to an isolated nucleic acid molecule that encodes a human β1A sodium channel subunit protein, said polynucleotide comprising a member selected from a group consisting of: (a) a polynucleotide having at least a 75% identity to a polynucleotide encoding a polypeptide consisting of amino acids 1 to 268 of SEQ.ID.NO.:14; (b) a polynucleotide having at least 75% identity to a polynucleotide encoding a polypeptide consisting of amino acids 150 to 268 of SEQ.ID.NO.:14; (c) a polynucleotide which is complementary to the polynucleotide of (a) or (b); and (d) a polynucleotide comprising at least 15 sequential bases of the polynucleotide of (a), (b), or (c). In one embodiment, the polynucleotide is RNA and in another embodiment, the polynucleotide is DNA. In another embodiment, the nucleotide sequence is selected from a group consisting of: (SEQ.ID.NO.:12) and (SEQ.ID.NO.:13). A further group includes isolated DNA molecules consisting of allelic variants, mutants, and functional derivatives of (SEQ.ID.NO.:12) and (SEQ.ID.NO.:13). In another embodiment, the isolated DNA molecule is genomic DNA.

The invention further relates to an expression vector for expression of a human β1A sodium channel subunit protein in a recombinant host, wherein said vector contains a recombinant gene encoding a human β1A sodium channel subunit protein and functional derivatives thereof. In one embodiment, the expression vector contains a cloned gene encoding a Human β1A sodium channel subunit protein, having a nucleotide sequence selected from a group consisting of: (SEQ.ID.NO.:12) and (SEQ.ID.NO.:13) and in another embodiment, the group further consists of allelic variants, mutants, and functional derivatives of SEQ.ID.NO.:12 and SEQ.ID.NO.:13. In another embodiment, the expression vector contains genomic DNA encoding a Human β1A sodium channel subunit protein.

The invention also relates to a recombinant host cell containing a recombinantly cloned gene encoding Human β1A sodium channel subunit protein or a functional derivative thereof. Preferably the gene has a nucleotide sequence selected from a group consisting of: (SEQ.ID.NO.:12); (SEQ.ID.NO.:13); and functional derivatives thereof. In another embodiment, the cloned gene is genomic DNA.

The invention also contemplates isolated protein encoded by a nucleic acid sequence capable of hybridizing under stringent hybridization conditions to a nucleotide sequence having the sequence of SEQ ID NO:12 or SEQ ID NO:13 that when combined with a Human α sodium channel subunit protein in a cell permits sodium ion flux in the cell. In one embodiment, the protein has an amino acid sequence selected from a group consisting of: (SEQ.ID.NO.:14) and functional derivatives thereof. The invention also contemplates antibodies that are specific to these proteins and monospecific antibodies, that is, antibodies that will only identify the human proteins of this invention, such as those antibodies that specifically recognize a human β1A sodium channel subunit protein.

The invention relates to a process for expression of a Human β1A sodium channel subunit protein in a recombinant host cell, comprising the steps of; (a) introducing an expression vector comprising a nucleic acid sequence capable of hybridizing under stringent hybridization conditions to a nucleotide sequence, or its complementary sequence, having the sequence of SEQ ID NO:12 or SEQ ID NO:13 into a cell; (b) culturing the cell of step (a) under conditions which allow expression of a protein encoded by the nucleotide sequence.

The invention further relates to a method of screening for a modulator of sodium channel activity comprising: (a) providing a cell that co-expresses a protein encoded by a nucleic acid capable of hybridizing under stringent hybridization conditions to a nucleotide sequence, or its complementary sequence, represented by SEQ ID NO:12 or SEQ ID NO:13 and a sodium channel α subunit protein wherein the cell elicits a sodium ion flux; (b) contacting the cell with a putative β1A modulating compound; and (c) measuring a change upon the cell that alters the sodium ion flux. In one embodiment of this method, at least one of the proteins is a recombinant protein. The the change in sodium ion flux is preferably selected from a group consisting of: (a) increasing the capacity to open the Na channel; (b) decreasing the capacity to open the Na channel; (c) increasing the rate of desensitization; (d) decreasing the rate of desensitization; (e) increasing the rate of re-sensitization of the channel; (f) decreasing the rate of re-sensitization of the channel; (g) increasing the level of β1A protein expression; (h) decreasing the level of β1A protein expression; (i) increasing the level of the α/β1A complex protein expression; and (j) decreasing the level of the α/β1A complex protein expression. Compounds identified by these methods are also contemplated within the scope of this invention as are pharmaceutical composition comprising these compounds.

The invention further relates to a number of methods for treating animals, including a method of treating neuropathic pain in a patient in need of such treatment comprising administration a compound of this invention. Methods for treating neuropathic pain in a patient in need of such treatment comprising altering the level of a human β1A subunit in a dorsal root ganglia cell in the patient are also contemplated in this invention.

The invention also relates to a method of treating chronic pain in a patient in need of such treatment comprising administering a compound of this invention as well as a method of treating febrile seizures in a patient in need of such treatment comprising administering a compound of this invention.

Methods for treating general epilepsy by administering a compound of this invention are contemplated as are anticonvulsant pharmaceutical composition comprising a compound of this invention. Further methods include a method of treating arrhythmia in a patient in need of such treatment comprising administering a compound identified by a method of this invention and methods for providing local anesthesia to a patient by administering a pharmaceutical composition comprising a compound of this invention. The invention further relates to a method for decreasing neuropathic pain in an individual comprising administering to said individual a modulator of a sodium channel β1A subunit in an amount effective to change the sodium channel activity in said individual and to methods for decreasing the expression of sodium channel β1A subunit in the cells of the individual. The invention also relates to a method for treating neuropathic pain in a subject comprising altering the level of sodium channel β1A subunits on the surface of a cell in the subject.

30. A method for decreasing neuropathic pain in a human comprising the step of administering a sodium channel β1A subunit-binding molecule to a sodium channel β1A subunit-expressing cell in the human.

BRIEF DESCRIPTION OF THE DRAWING

FIG. 1—The amino acid sequence of human voltage gated sodium channel β1A subunit (SEQ ID NO:14 in (A) and SEQ.ID.NO.:16 in (B)) aligned with (A) the rat voltage gated sodium channel β1A subunit and (SEQ ID NO:15) and (B) human voltage gated sodium channel β1 subunit (SEQ ID NO:17) are shown. The overall identity between human and rat VGSC β1A subunits is about 72%, while the identity of their carboxyl terminal regions is less than 33%. The overall identity of human VGSC β1A and β1 subunits is 75%, but the identity of their carboxyl terminal regions is less than 17%.

FIG. 4 illustrates the intensity of β1A labeling in DRG neurons in normal rats and in SNL rats at various times post-surgery. The bars shown represent labeling in nociceptive (open bars) and sensory (shaded bars) neurons. N=3-5 animals per group and 30-40 neurons of each type per animal. The intensity of the labeling in each neuronal type at each DRG level increased with time post surgery (see table 1 for statistical analysis).

FIG. 5 illustrates the intensity of β1 labeling in DRG neurons in normal rats and in SNL rats at various times post-surgery. The bars shown represent labeling in nociceptive (open bars) and sensory (shaded bars) neurons. N=3-5 animals per group and 30-40 neurons of each type per animal. The intensity of the labeling varied with the time post surgery (see table 1 for statistical results).

DETAILED DESCRIPTION

Definitions

Figure 2:
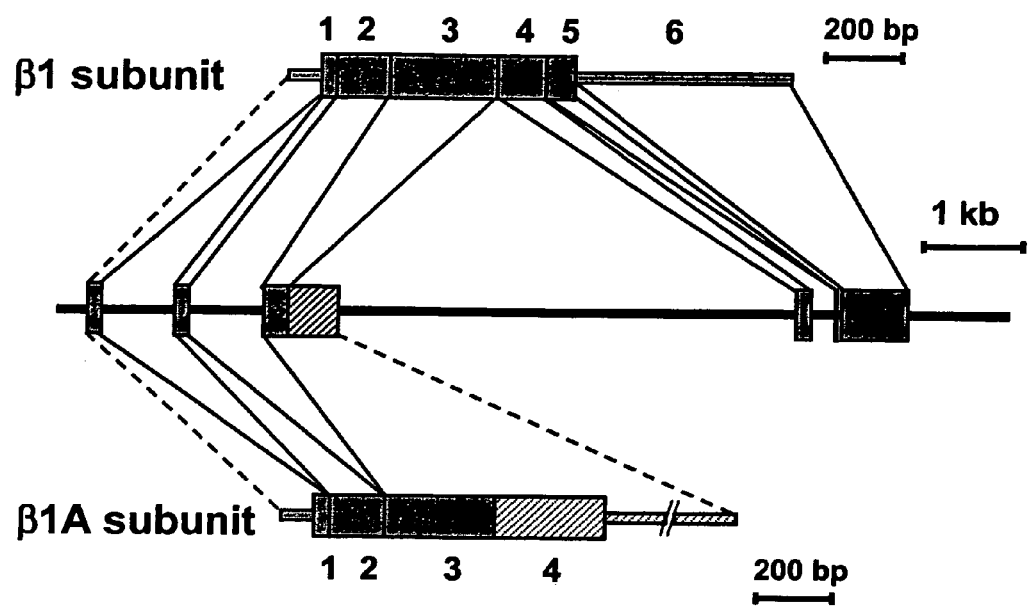
FIG. 2 illustrates the genomic and transcriptional organization of the human β1 gene (SCN1B). The gene encoding sodium channel β1 and β1A subunits spans about 9-10 kb on chromosome 19, containing seven exons (1, 2, 3, 4A, 4, 5, and 6) and five introns. An alternative exon 4A is located in the 5' region of the intron 3. The human β1 subunit is encoded by exon 1-3 and 4-6, while human β1A by exon 1-3 and exon 4A.

The term "protein domain" as used herein refers to a region of a protein that can fold into a stable three-dimensional structure independent of the rest of the protein. This structure may maintain a specific function within the protein including the site of enzymatic activity, creation of a recognition motif for another molecule, or provide necessary structural components for a protein to exist in a particular environment. Protein domains are usually evolutionarily conserved regions of proteins, both within a protein family and within protein superfamilies that perform similar functions. The term "protein superfamily" as used herein refers to proteins whose evolutionary relationship may not be entirely established or may be distant by accepted phylogenetic standards, but shows similar three dimensional structure or displays unique consensus of critical amino acids. The term "protein family" as used herein refers to proteins whose evolutionary relationship has been established by accepted phylogenic standards.

The term "fusion protein" as used herein refers to protein constructs that are the result of combining multiple protein domains or linker regions. Fusion proteins are most often created by molecular cloning of the nucleotide sequences to result in the creation of a new polynucleotide sequence that codes for the desired protein. Alternatively, creation of a fusion protein may be accomplished by chemically joining two proteins together.

The term "linker region" or "linker domain" or similar such descriptive terms as used herein refers to stretches of polynucleotide or polypeptide sequence that are used in the construction of a cloning vector or fusion protein. Functions of a linker region can include introduction of cloning sites into the nucleotide sequence, introduction of a flexible component or space-creating region between two protein domains, or creation of an affinity tag for specific molecule interaction. A linker region may be introduced into a fusion protein without a specific purpose, but results from choices made during cloning.

The term "cloning site" or "polycloning site" as used herein refers to a region of the nucleotide sequence contained within a cloning vector or engineered within a fusion protein that has one or more available restriction endonuclease consensus sequences. These nucleotide sequences can be introduced into other cloning vectors to facilitate cloning, the creation of novel fusion proteins, or they can be used to introduce specific site-directed mutations. It is well known by those in the art that cloning sites can be engineered at a desired location by silent mutation, conserved mutation, or introduction of a linker region that contains desired restriction enzyme consensus sequences. It is also well known by those in the art that the precise location of a cloning site can be flexible so long as the desired function of the protein or fragment thereof being cloned is maintained.

The term "tag" as used herein refers to a nucleotide sequence that encodes an amino acid sequence that facilitates isolation, purification or detection of a fusion protein containing the tag. A wide variety of such tags are known to those skilled in the art, and are suitable for use in the present invention. Suitable tags include, but are not limited to, HA peptide, polyhistidine peptides, biotin/avidin, and other antibody epitope binding sites.

Isolation of Human Voltage Gated Sodium Channel β1A Subunit Nucleic Acid

The voltage gated sodium channel is a multi-subunit protein complex containing a pore forming subunit α, and two regulatory subunits, β1 and β2. While the α subunit determines the basic properties of the channel, β1 and β2 subunits modulate almost all aspects of the channel properties including voltage dependent gating, voltage dependent activation and inactivation, and most strikingly, increasing functional channel density on the membrane. From molecular pharmacologic and electrophysiologic perspectives, there are more subtypes of voltage gated sodium channel in the excitable cells than cloned α subunits. This may be partially due to the existence of more α subunits in nature to be cloned and characterized. On the other hand, one might also expect that there might be more than one type of β1 and β2 subunits. In other words, the variety of voltage gated sodium channel may result from the different types of α subunit associating with one type of β1 and β2 subunits, and vice versa. In fact, biochemical study had revealed that there are more than one type of sodium channel β1 subunit as determined by Western blot with β1 specific antibody (Sutkowski, et al. 1990).

Recently β1A, a novel voltage-gated sodium channel subunit and splice variant of β1, has been cloned and was reported to increase sodium current density at the plasma membrane and change voltage dependent kinetics when co-expressed with αIIA subunits in CHL fibroblasts (Kazan-Gillespie et al., 2000). β1A is developmentally regulated in the brain. The subcellular distribution studies of rat VGSC β1A subunit demonstrated that it was altered in addition to being up-regulated in the DRG neurons as a consequence of peripheral nerve injury. Furthermore, rat VGSC β1A subunit may be important in the regulation of the aberrant array of sodium channels expressed subsequent to nerve injury.

To study the human β1A subunit, we first tried to clone the subunit using a homologous cloning strategy. Since β1A is an intron retained splicing variant at the carboxyl terminus of the β1 subunit, the forward primer was designed based on the human VGSC β1 subunit; while the reverse primer was designed based on rat VGSC β1A subunit. Unexpectedly, this pair of primers failed to amplify any DNA fragment from human adrenal gland, fetal brain and adult brain Marathon™ ready cDNA libraries. Three different reverse primers based on the sequence encoding the carboxyl terminus of rat β1A subunit were then designed. However, none of these primers paired with forward primer could amplify any DNA fragment from the above cDNA libraries under several PCR conditions, suggesting that human VGSC β1A subunit was significantly different from its counterpart in rat.

In order to clone the splicing variant of human VGSC β1A subunit, a Rapid Amplification of cDNA End (RACE-PCR) technique was used. Unlike regular RT-PCR that requires two gene specific primers, RACE-PCR requires only one specific primer pairing with a universal primer (AP1 or AP2) for RT-PCR amplification. This requires adding an adaptor recognized by the universal primer to the end of each cDNA when the library was made. Currently, this type of cDNA library is commercially available (Marathon™ ready cDNA library, Clontech). Therefore, by this technique, human VGSC β1A subunit could be amplified with a human β1 specific primer (SB1-10, see example 1) without knowing the sequence of human β1A carboxyl terminus. The technical difficulty of this application is to effectively distinguish novel β1A from the β1 subunit because of using β1 subunit specific primer for RACE-PCR. To solve this problem, the transformants were pre-screened by PCR with a pair of primers recognizing only the human VGSC β1 subunit and the negative clones (which could not be amplified by such PCR) would be subjected for further characterization and sequencing. With this strategy, a novel human VGSC β1A subunit was cloned from human adrenal gland Marathon™ ready cDNA library, and subsequently amplified from human fetal brain Marathon™ ready cDNA library with human β1A specific primers.

Analysis of the primary sequence revealed that the human VGSC β1A subunit is also a splicing variant of the β1 subunit with a retained intron and in frame stop codon. This novel VGSC β subunit also contains the basic structure of VGSC β subunit: an amino-terminal extracellular immunoglobulin-like motif and a carboxyl-terminal transmembrane domain. However, the human VGSC β1A subunit is significantly different from its rat counterpart. They share only about 35% identity at their carboxyl terminal coding region.

The present invention relates to DNA encoding human VGSC β1A subunit that was isolated from human VGSC β1A subunit producing cells. The term "Human VGSC β1A subunit", as used herein, refers to protein which can specifically function as a channel subunit. That is, it can combine with the other protein subunits to form a functioning calcium channel.

The recombinant protein is useful to identify modulators of the functional human VGSC β1A subunit. Northern blot analysis demonstrated that the VGSC β1A subunit was widely distributed in a variety tissues including, but not limited, in brain, heart, skeletal muscle, liver, lung, placenta, kidney and pancreas. In brain, the VGSC β1A subunit expresses most highly in the cerebellum region. Immunohistochemical study also demonstrates that the VGSC β1A was not only expressed in dorsal root ganglia (DRG), but is also up-regulated after nerve injury, suggesting it plays a role in neuropathic pain. Alteration in sodium channel expression and/or function can have a profound influence on the firing properties of peripheral and central neurons, and many other tissues. Modulators of VGSC β1A can be identified in the assays of this invention and tested for their use as therapeutic agents for neuropathic pain, chronic pain, febrile seizures and general epilepsy, local anesthetics, antiarrhythmics and anticonvulsants as well as many other human diseases related to sodium channels (Wallace, et al. 1998, Porreca, et al, 1999, Balser 1999). Human VGSC β1A may also be useful in human diseases where other β1 sodium channel alterations are linked to aberrant sodium channel activity, such as generalized epilepsy with febrile seizures plus (GEFS+) and congenital long-QT syndrome (LQT) (a cardiac arrhythmia characterized in part by prolonged ventricular repolarization).

Moreover, as provided in Example 12 below, the expression of the β1A subunit and β1 was investigated in DRG neurons from a nerve ligation model of neuropathic pain in rats using immunohistochemistry and image analysis. The levels of β1A subunit and β1 expression were increased most notably in the nociceptive DRG neurons, although there were increases in the sensory DRG neurons as well. However, the subcellular labeling of these two polypeptides differed dramatically in the DRG neurons subsequent to peripheral nerve injury. These studies demonstrated that peripheral nerve injury is associated with upregulation of β1A subunit and β1 sodium channel subunits and altered cellular distribution patterns of β1A in DRG. This is evidence that the sodium channel β1A subunit is important in the regulation of the aberrant sodium channel expression in DRG neurons subsequent to nerve injury.

Thus, this invention also contemplates the use of screening assays employing the human β1A subunit to identify modulators capable of binding to the β1A subunit. The modulators that are capable of binding to the human β1A subunit can then be used as a therapeutic, such as in a pharmaceutical composition, for the treatment of or as a method for decreasing neuropathic pain in a human. The pharmaceutical compositions comprising the modulator of the human β1A subunit are delivered to cells binding to a sodium channel β1A subunit-expressing cell in the human and function to decrease neuropathic pain.

A variety of cells and cell lines may be used to isolate Human β1A sodium channel subunit cDNA using primers selected based on the nucleotide sequence encoding the human β1A sodium channel subunit.

Any of a variety of procedures known in the art may be used to molecularly clone Human β1A sodium channel subunit DNA to obtain related sequences or allelic variants. These methods include, but are not limited to, direct functional expression of the Human β1A sodium channel subunit genes following the construction of a Human β1A sodium channel subunit-containing cDNA library in an appropriate expression vector system. Another method is to screen Human β1A sodium channel subunit-containing cDNA library constructed in a bacteriophage or plasmid shuttle vector with a labeled oligonucleotide probe designed from the amino acid sequence of the Human β1A sodium channel subunit subunits. An additional method consists of screening a Human β1A sodium channel subunit-containing cDNA library constructed in a bacteriophage or plasmid shuttle vector with a partial cDNA encoding the Human β1A sodium channel subunit protein. This partial cDNA is obtained by the specific PCR amplification of Human β1A sodium channel subunit DNA fragments through the design of degenerate oligonucleotide primers from the amino acid sequence of the purified Human β1A sodium channel subunit protein.

Another method is to isolate RNA from human VGSC β1A subunit-producing cells and translate the RNA into protein via an in vitro or an in vivo translation system. The translation of the RNA into a peptide a protein will result in the production of at least a portion of the Human β1A sodium channel subunit protein which can be identified by, for example, immunological reactivity with an anti-human β1A sodium channel subunit antibody or by biological activity of Human β1A sodium channel subunit protein. In this method, pools of RNA isolated from Human β1A sodium channel subunit-producing cells can be analyzed for the presence of an RNA that encodes at least a portion of the Human β1A sodium channel subunit protein. Further fractionation of the RNA pool results in purification of the Human β1A sodium channel subunit RNA from non-Human β1A sodium channel subunit RNA. The peptide or protein produced by this method may be analyzed to provide amino acid sequences which in turn are used to provide primers for production of Human β1A sodium channel subunit cDNA, or the RNA used for translation can be analyzed to provide nucleotide sequences encoding Human β1A sodium channel subunit and produce probes for this production of Human β1A sodium channel subunit cDNA. This method is known in the art and can be found in, for example, Maniatis, T., Fritsch, E. F., Sambrook, J. in *Molecular Cloning: A Laboratory Manual*, Second Edition, Cold Spring Harbor Laboratory Press, Cold Spring Harbor, N.Y. 1989.

It is readily apparent to those skilled in the art that suitable cDNA libraries may be prepared from cells or cell lines which have Human β1A sodium channel subunit activity. The selection of cells or cell lines for use in preparing a cDNA library to isolate Human β1A sodium channel subunit cDNA may be done by first measuring cell associated Human β1A sodium channel subunit activity using the measurement of Human β1A sodium channel subunit-associated biological activity or a ligand binding assay.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual, Second Edition (Cold Spring Harbor Laboratory, Cold Spring Harbor, N.Y., 1989).

It is also readily apparent to those skilled in the art that DNA encoding Human β1A sodium channel subunit may also be isolated from a suitable genomic DNA library. Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manual, Second Edition (Cold Spring Harbor Laboratory, Cold Spring Harbor, N.Y., 1989).

In order to clone the human sodium channel β1A subunit gene by the above methods, the amino acid sequence of Human sodium channel β1A subunit may be necessary. To accomplish this, Human β1A sodium channel subunit protein may be purified and partial amino acid sequence determined by automated sequencers. It is not necessary to determine the entire amino acid sequence, but the linear sequence of two regions of 6 to 8 amino acids from the protein is determined for the production of primers for PCR amplification of a partial Human β1A sodium channel subunit DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the Human β1A sodium channel subunit sequence but will be capable of hybridizing to Human β1A sodium channel subunit DNA even in the presence of DNA oligonucleotides with mismatches. The mismatched DNA oligonucleotides may still sufficiently hybridize to the Human sodium channel β1A subunit DNA to permit identification and isolation of Human sodium channel β1A subunit encoding DNA. DNA isolated by these methods can be used to screen DNA libraries from a variety of cell types, from invertebrate and vertebrate sources, and to isolate homologous genes.

Purified biologically active Human sodium channel β1A subunit may have several different physical forms. The Human sodium channel β1A subunit may exist as a full-length nascent or unprocessed polypeptide, or as partially processed polypeptides or combinations of processed polypeptides. The full-length nascent Human β1A sodium channel subunit polypeptide may be post-translationally modified by specific proteolytic cleavage events that results in the formation of fragments of the full length nascent polypeptide. A fragment or physical association of fragments may have the full biological activity associated with Human β1A sodium channel subunit however, the degree of Human β1A sodium channel subunit activity may vary between individual Human β1A sodium channel subunit fragments and physically associated Human β1A sodium channel subunit polypeptide fragments.

Because the genetic code is degenerate, more than one codon may be used to encode a particular amino acid, and therefore, the amino acid sequence can be encoded by any of a set of similar DNA oligonucleotides. Only one member of the set will be identical to the Human β1A sodium channel subunit sequence but will be capable of hybridizing to Human β1A sodium channel subunit DNA even in the presence of DNA oligonucleotides with mismatches under appropriate conditions. Under alternate conditions, the mismatched DNA oligonucleotides may still hybridize to the Human β1A sodium channel subunit DNA to permit identification and isolation of Human β1A sodium channel subunit encoding DNA.

DNA encoding Human β1A sodium channel subunit from a particular organism may be used to isolate and purify homologues of Human β1A sodium channel subunit from other organisms. To accomplish this, the first Human β1A sodium channel subunit DNA may be mixed with a sample containing DNA encoding homologues of Human β1A sodium channel subunit under appropriate hybridization conditions. The hybridized DNA complex may be isolated and the DNA encoding the homologous DNA may be purified therefrom.

Functional Derivatives/Variants

It is known that there is a substantial amount of redundancy in the various codons that code for specific amino acids. Therefore, this invention is also directed to those DNA sequences that contain alternative codons that code for the eventual translation of the identical amino acid. For purposes of this specification, a sequence bearing one or more replaced codons will be defined as a degenerate variation. Also included within the scope of this invention are mutations either in the DNA sequence or the translated protein, which do not substantially alter the ultimate physical properties of the expressed protein. For example, substitution of aliphatic amino acids Alanine, Valine, Leucine and Isoleucine; interchange of the hydroxyl residues Serine and Threonine, exchange of the acidic residues Aspartic acid and Glutamic acid, substitution between the amide residues Asparagine and Glutamine, exchange of the basic residues Lysine and Arginine and human β1A sodium channel subunits among the aromatic residues Phenylalanine, Tyrosine may not cause a change in functionality of the polypeptide. Such substitutions are well known and are described, for instance in *Molecular Biology of the Gene*, 4$^{th}$ Ed. Bengamin Cummings Pub. Co. by Watson et al.

It is known that DNA sequences coding for a peptide may be altered so as to code for a peptide having properties that are different than those of the naturally occurring peptide. Methods of altering the DNA sequences include, but are not limited to site directed mutagenesis, chimeric substitution, and gene fusions. Site-directed mutagenesis is used to change one or more DNA residues that may result in a silent mutation, a conservative mutation, or a nonconservative mutation. Chimeric genes are prepared by swapping domains of similar or different genes to replace similar domains in the human β1A sodium channel subunit gene. Similarly, fusion genes may be prepared that add domains to the human β1A sodium channel subunit gene, such as an affinity tag to facilitate identification and isolation of the gene. Fusion genes may be prepared to replace regions of the human β1A sodium channel subunit gene, for example to create a soluble version of the protein by removing a transmembrane domain or adding a targeting sequence to redirect the normal transport of the protein, or adding new post-translational modification sequences to the human β1A sodium channel subunit gene. Examples of altered properties include but are not limited to changes in the affinity of an enzyme for a substrate or a receptor for a ligand. All such changes of the polynucleotide or polypeptide sequences are anticipated as useful variants of the present invention so long as the original function of the polynucleotide or polypeptide sequence of the present invention is maintained as described herein.

IDENTITY or SIMILARITY, as known in the art, are relationships between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Both identity and similarity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity and similarity between two polynucleotide or two polypeptide sequences, both terms are well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., (1988) SIAM J. Applied Math., 48, 1073). Methods commonly employed to determine identity or similarity between sequences include, but are not limited to those disclosed in Carillo, H., and Lipman, D., (1988) SIAM J. Applied Math., 48, 1073. Preferred methods to determine identity are designed to give the largest match between the sequences tested. Methods to determine identity and similarity are codified in computer programs. Preferred computer program methods to determine identity and similarity between two sequences include, but are not limited to, GCG program package (Devereux, J., et al., (1984) Nucleic Acids Research 12(1), 387), BLASTP, BLASTN, and FASTA (Atschul, S. F. et al., (1990) J. Molec. Biol. 215, 403).

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. Polynucleotides embraces short polynucleotides often referred to as oligonucleotide(s).

The term polypeptides, as used herein, refers to the basic chemical structure of polypeptides that is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art.

Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W.H. Freeman and Company, New York (1993). Many detailed reviews are available on this subject, such as, for example, those provided by Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York (1983); Seifter et al., (1990) Meth. Enzymol. 182, 626-646 and Rattan et al., "Protein Synthesis: Posttranslational Modifications and Aging", (1992) Ann. N.Y. Acad. Sci. 663, 48-62.

It will be appreciated, as is well known and as noted above, that polypeptides are not always entirely linear. For instance, polypeptides may be generally as a result of posttranslational events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli or other cells, prior to proteolytic processing, almost invariably will be N-formylmethionine. During post-translational modification of the peptide, a methionine residue at the NH.sub.2-terminus may be deleted. Accordingly, this invention contemplates the use of both the methionine-containing and the methionine-less amino terminal variants of the protein of the invention.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as, for example, E. coli. Accordingly, when glycosylation is desired, a polypeptide should be expressed in a glycosylating host, generally a eukaryotic cell. Insect cells often carry out the same post-translational glycosylations as mammalian cells and, for this reason, insect cell expression systems have been developed to efficiently express mammalian proteins having native patterns of glycosylation, inter alia. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized recombinantly by expressing a polynucleotide in a host cell.

VARIANT(S) of polynucleotides or polypeptides, as the term is used herein, are polynucleotides or polypeptides that differ from a reference polynucleotide or polypeptide, respectively. A variant of the polynucleotide may be a naturally occurring variant such as a naturally occurring allelic variant, or it may be a variant that is not known to occur naturally. A polynucleotide variant is a polynucleotide that differs in nucleotide sequence from another, reference polynucleotide. Generally, differences are limited so that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed above.

A polypeptide variant is a polypeptide that differs in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination. As used herein, a "functional derivative" of Human β1A sodium channel subunit is a compound that possesses a biological activity (either functional or structural) that is substantially similar to the biological activity of Human β1A sodium channel subunit. The term "functional derivatives" is intended to include the "fragments," "variants," "degenerate variants," "analogs" and "homologues" or to "chemical derivatives" of Human β1A sodium channel subunit. Useful chemical derivatives of polypeptide are well known in the art and include, for example, covalent modification of one or more reactive organic sites contained within the polypeptide with a secondary chemical moiety.

Well known cross-linking reagents are useful to react to amino, carboxyl, or aldehyde residues to introduce, for example, an affinity tag such as biotin, a fluorescent dye, or to conjugate the polypeptide to a solid phase surface (for example to create an affinity resin). The term "fragment" is meant to refer to any polypeptide subset of the Human β1A sodium channel subunit.

A molecule is "substantially similar" to a Human β1A sodium channel subunit if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire Human β1A sodium channel subunit molecule or to a fragment thereof. Further particularly preferred in this regard are polynucleotides encoding variants, analogs, derivatives and fragments of SEQ.ID.NO.:13, and variants, analogs and derivatives of the fragments, which have the amino acid sequence of the polypeptide of SEQ.ID.NO.:14 in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the gene of SEQ.ID.NO.:13. Also especially preferred in this regard are conservative substitutions. Most highly preferred are polynucleotides encoding polypeptides having the amino acid sequence of SEQ.ID.NO.:14, without substitutions.

Further preferred embodiments of the invention are polynucleotides that are at least 75% identical over their entire length to a polynucleotide encoding the polypeptide having the amino acid sequence set out in SEQ.ID.NO.:14, and polynucleotides which are complementary to such polynucleotides. Yet other preferred embodiments of the invention are polynucleotides that are at least 75% identical over a consecutive portion of their length to a polynucleotide encoding the polypeptide having the amino acid sequence 150 to 268 set out in SEQ.ID.NO.:14, and polynucleotides which are complementary to such polynucleotides. Alternatively, highly preferred are polynucleotides that comprise a region that is at least 80% identical, more highly preferred are polynucleotides at comprise a region that is at least 90% identical, and among these preferred polynucleotides, those with at least 95% are especially preferred. Furthermore, those with at least 97% identity are highly preferred among those with at least 95%, and among these those with at least 98% and at least 99% are particularly highly preferred, with at least 99% being the most preferred. The polynucleotides, which hybridize to the polynucleotides described herein, in a preferred embodiment, encode polypeptides, which retain substantially the same biological function or activity as the polypeptide characterized by the deduced amino acid sequence of SEQ.ID.NO.:14. Preferred embodiments in this respect, moreover, are polynucleotides that encode polypeptides that retain substantially the same biological function or activity as the mature polypeptide encoded by the DNA of SEQ.ID.NO.:13. The present invention further relates to polynucleotides that hybridize to the herein above-described sequences. In this regard, the present invention especially relates to polynucleotides that hybridize under stringent conditions to the herein above-described polynucleotides. As herein used, the term "stringent conditions" means hybridization will occur only if there is at least 95% and preferably at least 97% identity between the sequences.

There are a large numbers of polynucleotide hybridization techniques known in the art including hybridizations coupling DNA to DNA, RNA to RNA and RNA to DNA. All of these methods can incorporate stringent hybridization conditions to facilitate the accurate identification of nucleic acid targeting to a hybridizable probe. As is known in the art, methods vary depending on the substrate used for hybridization and Maniatis et al. supra, as well as a variety of references in the art detail a number of stringent hybridization techniques. In one example, DNA or RNA samples to be probed are immobilized on a suitable substrate such as nitrocellulose, nylon, polyvinylidene difluoride, or the like. A purified probe, preferably with sufficient specific activity (generally greater than about $10^8$ cpm/μg probe), substantially free of contaminating DNA, protein or unincorporated nucleotides is used. Where nitrocellulose is used, and the immobilized nucleic acid is DNA immobilized on nitrocellulose, the nitrocellulose with DNA is incubated with a hybridization solution comprising 50% formamide-deionized, 6×SSC, 1% SDS, 0.1% Tween 20 and 100 μg/ml t RNA at 42° C. for 15 minutes. Probe is added and the nitrocellulose is further immobilized at 42° C. for about 12-19 hours. The nitrocellulose is then washed in at least two successive washes at 22° C. followed by stringent washes at 65° C. in a buffer of 0.04M sodium phosphate, pH 7.2, 1% SDS and 1 mM EDTA. Conditions for increasing the stringency of a variety of nucleotide hybridizations are well known in the art.

As discussed additionally herein regarding polynucleotide assays of the invention, for instance, polynucleotides of the invention may be used as a hybridization probe for RNA, cDNA and genomic DNA to isolate full-length cDNAs and genomic clones encoding the sequences of SEQ.ID.NO.:13 and to isolate cDNA and genomic clones of other genes that have a high sequence similarity to SEQ.ID.NO.:13. Such probes generally will comprise at least 15 bases. Preferably, such probes will have at least 30 bases and may have at least 50 bases. Particularly preferred probes will have at least 30 bases and will have 50 bases or less. For example, the coding region of the gene of the invention may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine to which members of the library the probe hybridizes.

The polypeptides of the present invention include the polypeptide of SEQ.ID.NO.:14 (in particular the mature polypeptide) as well as polypeptides which have at least 75% identity to the polypeptide of SEQ.ID.NO.:14, preferably at least 80% identity to the polypeptide of SEQ.ID.NO.:14, and more preferably at least 90% similarity (more preferably at least 90% identity) to the polypeptide of SEQ.ID.NO.:14 and still more preferably at least 95% similarity (still more preferably at least 95% identity) to the polypeptide of SEQ.ID.NO.:14 and also include portions of such polypeptides with such portion of the polypeptide generally containing at least 30 amino acids and more preferably at least 50 amino acids. Representative examples of polypeptide fragments of the invention, include, for example, truncation polypeptides of SEQ.ID.NO.:14.

Truncation polypeptides include polypeptides having the amino acid sequence of SEQ.ID.NO.:14, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Also preferred in this aspect of the invention are fragments characterized by structural or functional attributes of the polypeptide characterized by the sequences of SEQ.ID.NO.:14. Preferred embodiments of the invention in this regard include fragments that comprise α-helix and α-helix forming regions, β-sheet and β-sheet-forming regions, turn and turn-forming regions, coil and coil-forming regions, hydrophilic regions, hydrophobic regions, α amphipathic regions, β amphipathic regions, flexible regions, surface-forming regions, substrate binding region, high antigenic index regions of the polypeptide of the invention, and combinations of such fragments. Preferred regions are those that mediate activities of the polypeptides of the invention. Most highly preferred in this regard are fragments that have a chemical, biological or other activity of the response regulator polypeptide of the invention, including those with a similar activity or an improved activity, or with a decreased undesirable activity.

Recombinant Expression of Human β1A Sodium Channel Subunit

The cloned Human β1A sodium channel subunit DNA obtained through the methods described herein may be recombinantly expressed by molecular cloning into an expression vector containing a suitable promoter and other appropriate transcription regulatory elements, and transferred into prokaryotic or eukaryotic host cells to produce recombinant Human β1A sodium channel subunit protein. Techniques for such manipulations are fully described in Maniatis, T. et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria including *E. coli*, bluegreen algae, plant cells, insect cells, fungal cells including yeast cells, and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency. Expression vectors may include, but are not limited to, cloning vectors, modified cloning vectors, specifically designed plasmids or viruses.

A variety of mammalian expression vectors may be used to express recombinant Human β1A sodium channel subunit in mammalian cells. Commercially available mammalian expression vectors which may be suitable for recombinant Human β1A sodium channel subunit expression, include but are not limited to, pMAMneo (Clontech), pIRES vectors (Clontech), pTET-On and pTET-Off (Clontech), pcDNA3 (Invitrogen), pMC1neo (Stratagene), pXT1 (Stratagene), pSG5 (Stratagene), EBO-pSV2-neo (ATCC 37593, ATCC, Manassas, Va.) pBPV-1(8-2) (ATCC 37110), pdBPV-MMT-neo (342-12) (ATCC 37224), pRSVgpt (ATCC 37199), pRS-Vneo (ATCC 37198), pSV2-dhfr (ATCC 37146), pUCTag (ATCC 37460), and IZD35 (ATCC 37565).

A variety of bacterial expression vectors may be used to express recombinant Human β1A sodium channel subunit in bacterial cells. Commercially available bacterial expression vectors which may be suitable for recombinant Human β1A sodium channel subunit expression include, but are not limited to, pET vectors (Novagen), pGEX vectors (Pharmacia) and pQE vectors (Qiagen).

A variety of fungal cell expression vectors may be used to express recombinant Human β1A sodium channel subunit in fungal cells such as yeast. Commercially available fungal cell expression vectors which may be suitable for recombinant Human β1A sodium channel subunit expression include but are not limited to pYES2 (Invitrogen) and *Pichia* expression vector (Invitrogen).

A variety of insect cell expression vectors may be used to express recombinant Human β1A sodium channel subunit in insect cells. Commercially available insect cell expression vectors which may be suitable for recombinant expression of Human β1A sodium channel subunit include, but are not limited to, pBlueBacHII (Invitrogen).

DNA encoding Human β1A sodium channel subunit may be cloned into an expression vector for expression in a recombinant host cell. Recombinant host cells may be prokaryotic or eukaryotic, including, but not limited to, bacteria such as *E. coli*, fungal cells such as yeast, mammalian cells including, but not limited to, cell lines of human, bovine, porcine, monkey and rodent origin, and insect cells including, but not limited to, *drosophila* and silkworm derived cell lines. Cell lines derived from mammalian species which may be suitable and which are commercially available, include, but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, HEK-293 (ATCC CRL1573), PC12 (ATCC CRL-1721).

The expression vector may be introduced into host cells via any one of a number of techniques including, but not limited to, transformation, transfection, protoplast fusion, lipofection, and electroporation. The expression vector-containing cells are clonally propagated and individually analyzed to determine whether they produce Human sodium channel β1A subunit protein. Identification of Human β1A sodium channel subunit expressing host cell clones may be done by several means, including but not limited to immunological reactivity with anti-human β1A sodium channel subunit antibodies, and the presence of host cell-associated Human β1A sodium channel subunit activity.

Expression of Human sodium channel β1A subunit DNA may also be performed using in vitro produced synthetic mRNA. Synthetic mRNA or mRNA isolated from Human β1A sodium channel subunit producing cells can be efficiently translated in various cell-free systems including, but not limited to, wheat germ extracts and reticulocyte extracts, as well as efficiently translated in cell based systems including, but not limited to, microinjection into frog oocytes, with microinjection into frog oocytes being generally preferred.

To determine the Human β1A sodium channel subunit DNA sequence(s) that yields optimal levels of Human β1A sodium channel subunit activity and/or Human β1A sodium channel subunit protein, Human β1A sodium channel subunit DNA molecules including, but not limited to, the following can be constructed: the full-length open reading frame of the Human β1A sodium channel subunit cDNA encoding the 32 kDa protein from approximately base 4 to approximately base 808 (these numbers correspond to first nucleotide of first methionine and last nucleotide before the first stop codon) and several constructs containing portions of the cDNA encoding Human β1A sodium channel subunit protein. All constructs can be designed to contain none, all or portions of the 5' or the 3' untranslated region of Human β1A sodium channel subunit cDNA. Human β1A sodium channel subunit activity and levels of protein expression can be determined following the introduction, both singly and in combination, of these constructs into appropriate host cells. Following determination of the Human β1A sodium channel subunit DNA cassette yielding optimal expression in transient assays, this Human β1A sodium channel subunit DNA construct is transferred to a variety of expression vectors, for expression in host cells including, but not limited to, mammalian cells, baculovirus-infected insect cells, *E. coli*, and the yeast *S. cerevisiae*.

Assay Methods for Human β1A Sodium Channel Subunit

Host cell transfectants and microinjected oocytes may be used to assay both the levels of functional Human β1A sodium channel subunit activity and levels of total Human β1A sodium channel subunit protein by the following methods. In the case of recombinant host cells, this involves the co-transfection of one or possibly two or more plasmids, containing the Human sodium channel β1A subunit DNA encoding one or more fragments or subunits. In the case of oocytes, this involves the co-injection of synthetic RNAs for Human sodium channel β1A subunit protein. Following an appropriate period of time to allow for expression, cellular protein is metabolically labeled with, for example $^{35}$S-methionine for 24 hours, after which cell lysates and cell culture supernatants are harvested and subjected to immunoprecipitation with polyclonal antibodies directed against the Human β1A sodium channel subunit protein.

Levels of Human β1A sodium channel subunit protein in host cells are quantitated by immunoaffinity and/or ligand affinity techniques. Cells expressing Human β1A sodium channel subunit can be assayed for the number of Human β1A sodium channel subunit molecules expressed by measuring the amount of radioactive [ligand] binding to cell membranes. Human β1A sodium channel subunit-specific affinity beads or Human β1A sodium channel subunit-specific antibodies are used to isolate for example $^{35}$S-methionine labeled or unlabelled Human β1A sodium channel subunit protein. Labeled Human β1A sodium channel subunit protein is analyzed by SDS-PAGE. Unlabelled Human β1A sodium channel subunit protein is detected by Western blotting, ELISA or RIA assays employing Human β1A sodium channel subunit specific antibodies.

Other methods for detecting Human β1A sodium channel subunit activity involve the direct measurement of Human β1A sodium channel subunit activity in whole cells transfected with Human β1A sodium channel subunit cDNA or oocytes injected with Human β1A sodium channel subunit mRNA and optionally a sodium channel subunit mRNA. Human β1A sodium channel subunit activity is measured by biological characteristics of the host cells expressing Human β1A sodium channel subunit DNA. In the case of recombinant host cells expressing Human β1A sodium channel subunit patch voltage clamp techniques can be used to measure channel activity and quantify modification of a sodium channel subunit ion flux as a function of Human β1A sodium channel subunit protein. In the case of oocytes patch clamp as well as two-electrode voltage clamp techniques can be used to measure sodium channel activity and quantify Human β1A sodium channel subunit protein.

Cell Based Assays

The present invention provides a whole cell or isolated cell membrane method to detect compound modulation of human β1A sodium channel subunit. The method comprises the steps;

1) contacting a compound, and a cell or isolated cell membrane that contains functional human β1A sodium channel subunit, and 2) measuring a change in the cell or isolated cell membrane in response to modified human β1A sodium channel subunit function by the compound.

The amount of time necessary for cell or cell membrane contact with the compound is empirically determined, for example, by running a time course with a known human β1A sodium channel subunit modulator and measuring cellular changes as a function of time.

The measurement means of the method of the present invention can be further defined by comparing a cell or cell membrane that has been exposed to a compound to an identical cell or cell membrane preparation that has not been similarly expose to the compound. Alternatively two cells, one containing functional human β1A sodium channel subunit and a second cell identical to the first, but lacking functional human β1A sodium channel subunit could be both used. Both cells or cell membranes are contacted with the same compound and compared for differences between the two cells. This technique is also useful in establishing the background noise of these assays. One of average skill in the art will appreciate that these control mechanisms also allow easy selection of cellular changes that are responsive to modulation of functional human β1A sodium channel subunit.

Particularly preferred cell based assays (or cell membrane assays, if suitable) are those where the cell expresses an endogenous or recombinant sodium α channel subunit simultaneously with recombinant human β1A. In these assays, a putative modulating compound can be analyzed for its effect on electrophysiological changes to the sodium flux upon the cell for altered expression of β1A expression, or altered expression of the α/β1A complex. Cells expressing recombinant human β1A are subjected to electrophysiological analysis to measure the total influx of sodium ions (Na$^+$) across the cell membrane by way of voltage differential using techniques well known by artisans in the field and described herein, including patch clamp voltage techniques as well as membrane proximal voltage sensitive dyes. Compounds that affect the proper function of human β1 may increase or decrease the capacity to open the Na channel, may increase or decrease the rate of Na influx (thus affect the change of membrane potential), may increase or decrease the rate of desensitization or re-sensitization of the channel. The term "test compound" or "modulating compound" as used herein in connection with a suspected modulator of human β1A refers to an organic molecule that has the potential to disrupt specific ion channel activity or cell surface expression of human β1A. For example, but not to limit the scope of the current invention, compounds may include small organic molecules, synthetic or natural amino acid peptides, proteins, or synthetic or natural nucleic acid sequences, or any chemical derivatives of the aforementioned.

The term "cell" refers to at least one cell, but includes a plurality of cells appropriate for the sensitivity of the detection method. Cells suitable for the present invention may be bacterial, yeast, or eukaryotic. For assays to which electrophysiological analysis is conducted, the cells must be eukaryotic, preferably selected from a group consisting of *Xenopus* oocytes, or PC12, COS-7, CHO, HEK293, SK-N-SH cells.

The assay methods to determine compound modulation of functional human sodium channel β1A subunit can be in conventional laboratory format or adapted for high throughput. The term "high throughput" refers to an assay design that allows easy analysis of multiple samples simultaneously, and capacity for robotic manipulation. Another desired feature of high throughput assays is an assay design that is optimized to reduce reagent usage, or minimize the number of manipulations in order to achieve the analysis desired. Examples of assay formats include 96-well or 384-well plates, levitating droplets, and "lab on a chip" microchannel chips used for liquid handling experiments. It is well known by those in the art that as miniaturization of plastic molds and liquid handling devices are advanced, or as improved assay devices are designed, that greater numbers of samples may be performed using the design of the present invention.

The cellular changes suitable for the method of the present invention comprise directly measuring changes in the function or quantity of human β1A sodium channel subunit, or by measuring downstream effects of human β1A sodium channel subunit function, for example by measuring secondary messenger concentrations or changes in transcription or by changes in protein levels of genes that are transcriptionally influenced by human β1A sodium channel subunit, or by measuring phenotypic changes in the cell. Preferred measurement means include changes in the quantity of human β1A sodium channel subunit protein, changes in the functional activity of human β1A sodium channel subunit, changes in the quantity of mRNA, changes in intracellular protein, changes in cell surface protein, or secreted protein, or changes in Ca+2, cAMP or GTP concentration. Changes in the quantity or functional activity of human β1A sodium channel subunit are described herein. Changes in the levels of mRNA are detected by reverse transcription polymerase chain reaction (RT-PCR) or by differential gene expression. Immunoaffinity, ligand affinity, or enzymatic measurement quantitated changes in levels of protein in host cells. Protein-specific affinity beads or specific antibodies are used to isolate for example $^{35}$S-methionine labeled or unlabelled protein. Labeled protein is analyzed by SDS-PAGE. Unlabelled protein is detected by Western blotting, cell surface detection by fluorescent cell sorting, cell image analysis, ELISA or RIA employing specific antibodies. Where the protein is an enzyme, the induction of protein is monitored by cleavage of a fluorogenic or colorimetric substrate.

Preferred detection means for cell surface protein include flow cytometry or statistical cell imaging. In both techniques the protein of interest is localized at the cell surface, labeled with a specific fluorescent probe, and detected via the degree of cellular fluorescence. In flow cytometry, the cells are analyzed in a solution, whereas in cellular imaging techniques, a field of cells is compared for relative fluorescence.

A preferred detection means for secreted proteins that are enzymes such as alkaline phosphatase or proteases, would be fluorescent or colorimetric enzymatic assays. Fluorescent/luminescent/color substrates for alkaline phosphatase are commercially available and such assays are easily adaptable to high throughput multiwell plate screen format. Fluorescent energy transfer based assays are used for protease assays. Fluorophore and quencher molecules are incorporated into the two ends of the peptide substrate of the protease. Upon cleavage of the specific substrate, separation of the fluorophore and quencher allows the fluorescence to be detectable. When the secreted protein could be measured by radioactive methods, scintillation proximity technology could be used. The substrate of the protein of interest is immobilized either by coating or incorporation on a solid support that contains a fluorescent material. A radioactive molecule, brought in close proximity to the solid phase by enzyme reaction, causes the fluorescent material to become excited and emit visible light. Emission of visible light forms the basis of detection of successful ligand/target interaction, and is measured by an appropriate monitoring device. An example of a scintillation proximity assay is disclosed in U.S. Pat. No. 4,568,649, issued Feb. 4, 1986. Materials for these types of assays are commercially available from Dupont NEN® (Boston, Mass.) under the trade name FlashPlate™.

A preferred detection means where the endogenous gene results in phenotypic cellular structural changes is statistical image analysis the cellular morphology or intracellular phenotypic changes. For example, but not by way of limitation, a cell may change morphology such a rounding versus remaining flat against a surface, or may become growth-surface independent and thus resemble transformed cell phenotype well known in the art of tumor cell biology, or a cell may produce new outgrowths. Phenotypic changes that may occur intracellularly include cytoskeletal changes, alteration in the endoplasmic reticulum/Golgi complex in response to new gene transcription, or production of new vesicles.

Where the endogenous gene encodes a soluble intracellular protein, changes in the endogenous gene may be measured by changes of the specific protein contained within the cell lysate. The soluble protein may be measured by the methods described herein.

The present invention is also directed to methods for screening for compounds that modulate the expression of DNA or RNA encoding Human β1A sodium channel subunit as well as the function of Human β1A sodium channel subunit protein in vivo. Compounds may modulate by increasing or attenuating the expression of DNA or RNA encoding a Human β1A sodium channel subunit, or the function of a Human β1A sodium channel subunit protein. Compounds that modulate the expression of DNA or RNA encoding a Human β1A sodium channel subunit or the function of a Human β1A sodium channel subunit protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are useful as candidate therapeutic agents.

Purification of Human β1A Sodium Channel Subunit Protein

Following expression of the Human β1A sodium channel subunit in a recombinant host cell, the Human β1A sodium channel subunit protein may be recovered to provide the purified Human β1A sodium channel subunit in active form. Several Human β1A sodium channel subunit purification procedures are available and suitable for use. As described above for purification of Human β1A sodium channel subunit from natural sources a recombinant Human β1A sodium channel subunit may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography, lectin chromatography, and antibody/ligand affinity chromatography.

Recombinant Human sodium channel β1A subunits can be separated from other cellular proteins through the use of an immunoaffinity column made with monoclonal or polyclonal antibodies specific for full length nascent Human β1A sodium channel subunit, polypeptide fragments of Human β1A sodium channel subunit or Human β1A sodium channel subunits. The affinity resin is then equilibrated in a suitable buffer, for example phosphate buffered saline (pH 7.3), and the cell culture supernatants or cell extracts containing a Human β1A sodium channel subunit or Human β1A sodium channel subunit subunits are slowly passed through the column. The column is then washed with the buffer until the optical density ($A_{280}$) falls to background, then the protein is eluted by changing the buffer condition, such as by lowering the pH using a buffer such as 0.23 M glycine-HCl (pH 2.6). The purified Human sodium channel β1A subunit protein is then dialyzed against a suitable buffer such as phosphate buffered saline.

Protein Based Assay

The present invention provides an in vitro protein assay method to detect compound modulation of human sodium channel β1A subunit protein activity. The method comprises the steps;

1) contacting a compound and a human β1A sodium channel subunit protein, and 2) measuring a change to human β1A sodium channel subunit function by the compound.

The amount of time necessary for cellular contact with the compound is empirically determined, for example, by running a time course with a known human sodium channel β1A subunit modulator and measuring changes as a function of time.

Production and Use of Antibodies that Bind to Human β1A Sodium Channel Subunit

Monospecific antibodies to Human β1A sodium channel subunit are purified from mammalian antisera containing antibodies reactive against Human β1A sodium channel subunit or are prepared as monoclonal antibodies reactive with Human β1A sodium channel subunit using the technique originally described by Kohler and Milstein, *Nature* 256: 495-497 (1975). Immunological techniques are well known in the art and described in, for example, *Antibodies: A laboratory manual* published by Cold Spring Harbor Laboratory Press, Cold Spring Harbor, N.Y., ISBN 0879693142. Monospecific antibody as used herein is defined as a single antibody species or multiple antibody species with homogenous binding characteristics for the human sodium channel β1A subunit. "Homogenous binding" as used herein refers to the ability of the antibody species to bind to a specific antigen or epitope, such as those associated with the Human β1A sodium channel subunit, as described above. Human β1A sodium channel subunit specific antibodies are raised by immunizing animals such as mice, rats, guinea pigs, rabbits, goats, horses and the like, with rabbits being preferred, with an appropriate concentration of Human β1A sodium channel subunit either with or without an immune adjuvant.

Preimmune serum is collected prior to the first immunization. Each animal receives between about 0.001 mg and about 1000 mg of human sodium channel β1A subunit associated with an acceptable immune adjuvant. Such acceptable adjuvants include, but are not limited to, Freund's complete, Freund's incomplete; alum-precipitate, water in oil emulsion containing *Corynebacterium parvum* and tRNA. The initial immunization consists of human sodium channel β1A subunit in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three-week intervals until maximal titers are obtained. At about 7 days after each booster immunization or about weekly after a single immunization, the animals are bled, the serum collected, and aliquots are stored at about −20° C.

Monoclonal antibodies (mAb) reactive with Human β1A sodium channel subunit are prepared by immunizing inbred mice, preferably Balb/c, with Human β1A sodium channel subunit. The mice are immunized by the IP or SC route with about 0.001 mg to about 1.0 mg, preferably about 0.1 mg, of Human β1A sodium channel subunit in about 0.1 ml buffer or saline incorporated in an equal volume of an acceptable adjuvant, as discussed above. Freund's adjuvant is preferred, with Freund's complete adjuvant being used for the initial immunization and Freund's incomplete adjuvant used thereafter. The mice receive an initial immunization on day 0 and are rested for about 2 to about 30 weeks. Immunized mice are given one or more booster immunizations of about 0.001 to about 1.0 mg of Human β1A sodium channel subunit in a buffer solution such as phosphate buffered saline by the intravenous (IV) route.

Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions that will allow the formation of stable hybridomas. Fusion partners may include, but are not limited to: mouse myelomas P3/NS1/Ag 4-1; MPC-11; S-194 and Sp2/0, with Sp2/0 being generally preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) or ELISA using Human β1A sodium channel subunit as the antigen. The culture fluids can also be tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973 or by the technique of limited dilution.

Monoclonal antibodies are produced in vivo by injection of pristane primed Balb/c mice, approximately 0.5 ml per mouse, with about $1\times10^6$ to about $6\times10^6$ hybridoma cells at least about 4 days after priming. Ascites fluid is collected at approximately 8-12 days after cell transfer and the monoclonal antibodies are purified by techniques known in the art.

In vitro production of anti-Human β1A sodium channel subunit mAb is carried out by growing the hybridoma in tissue culture media well known in the art. High density in vitro cell culture may be conducted to produce large quantities of anti-human β1A sodium channel subunit mAbs using hollow fiber culture techniques, air lift reactors, roller bottle, or spinner flasks culture techniques well known in the art. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of Human β1A sodium channel subunit in body fluids or tissue and cell extracts.

It is readily apparent to those skilled in the art that the above described methods for producing monospecific antibodies may be utilized to produce antibodies specific for Human β1A sodium channel subunit polypeptide fragments, or full-length nascent Human β1A sodium channel subunit polypeptide, or the individual Human β1A sodium channel subunit subunits. Specifically, it is readily apparent to those skilled in the art that monospecific antibodies may be generated which are specific for only one Human β1A sodium channel subunit or the fully functional human β1A sodium channel subunit protein. It is also apparent to those skilled in the art that monospecific antibodies may be generated that inhibit normal function of human β1A sodium channel subunit protein.

Human β1A sodium channel subunit antibody affinity columns are made by adding the antibodies to a gel support such that the antibodies form covalent linkages with the gel bead support. Preferred covalent linkages are made through amine, aldehyde, or sulfhydryl residues contained on the antibody. Methods to generate aldehydes or free sulfhydryl groups on antibodies are well known in the art; amine groups are reactive with, for example, N-hydroxysuccinimide esters.

Kit Compositions Containing Human β1A Sodium Channel Subunit Specific Reagents

Kits containing Human β1A sodium channel subunit DNA or RNA, antibodies to Human β1A sodium channel subunit, or Human β1A sodium channel subunit protein may be prepared. Such kits are used to detect DNA which hybridizes to Human β1A sodium channel subunit DNA or to detect the presence of Human β1A sodium channel subunit protein or peptide fragments in a sample. Such characterization is useful for a variety of purposes including, but not limited to, forensic analyses, diagnostic applications, and epidemiological studies.

The DNA molecules, RNA molecules, recombinant protein and antibodies of the present invention may be used to screen and measure levels of Human β1A sodium channel subunit DNA, Human β1A sodium channel subunit RNA or Human β1A sodium channel subunit protein. The recombinant proteins, DNA molecules, RNA molecules and antibodies lend themselves to the formulation of kits suitable for the detection and typing of Human β1A sodium channel subunit. Such a kit would comprise a compartmentalized carrier suitable to hold in close confinement at least one container. The carrier would further comprise reagents such as recombinant Human β1A sodium channel subunit protein or anti-human β1A sodium channel subunit antibodies suitable for detecting Human β1A sodium channel subunit. The carrier may also contain a means for detection such as labeled antigen or enzyme substrates or the like.

Gene Therapy

Nucleotide sequences that are complementary to the Human β1A sodium channel subunit encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other Human β1A sodium channel subunit antisense oligonucleotide mimetics. Human β1A sodium channel subunit antisense molecules may be introduced into cells by microinjection, liposome encapsulation or by expression from vectors harboring the antisense sequence. Human β1A sodium channel subunit antisense therapy may be particularly useful for the treatment of diseases where it is beneficial to reduce Human β1A sodium channel subunit activity.

Human β1A sodium channel subunit gene therapy may be used to introduce Human β1A sodium channel subunit into the cells of target organisms. The Human β1A sodium channel subunit gene can be ligated into viral vectors that mediate transfer of the Human β1A sodium channel subunit DNA by infection of recipient host cells. Suitable viral vectors include retrovirus, adenovirus, adeno-associated virus, herpes virus, vaccinia virus, polio virus and the like. Alternatively, Human β1A sodium channel subunit DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo Human β1A sodium channel subunit gene therapy. Human β1A sodium channel subunit gene therapy may be particularly useful for the treatment of diseases where it is beneficial to elevate Human β1A sodium channel subunit activity. Protocols for molecular methodology of gene therapy suitable for use with the human β1A sodium channel subunit gene is described in *Gene Therapy Protocols*, edited by Paul D. Robbins, Human press, Totawa N.J., 1996.

Pharmaceutical Compositions

Pharmaceutically useful compositions comprising Human β1A sodium channel subunit DNA, Human, β1A sodium channel subunit RNA, or Human β1A sodium channel subunit protein, or modulators of Human β1A sodium channel subunit receptor activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders in which modulation of Human β1A sodium channel subunit-related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the Human β1A sodium channel subunit receptor or its activity while minimizing any potential toxicity. In addition, co-administration or sequential administration of other agents may be desirable.

The present invention also has the objective of providing suitable topical, oral, systemic and parenteral pharmaceutical formulations for use in the novel methods of treatment of the present invention. The compositions containing compounds or modulators identified according to this invention as the active ingredient for use in the modulation of Human β1A sodium channel subunit can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a Human β1A sodium channel subunit modulating agent.

The daily dosage of the products may be varied over a wide range from 0.01 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the Human β1A sodium channel subunit receptor modulators are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators of the present invention may be administered in a single daily dose, or the total daily dosage may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds or modulators of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds or modulators herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or β-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that may be employed include glycerin and the like. For parenteral administration, sterile suspensions and solutions are desired. Isotonic preparations, which generally contain suitable preservatives, are employed when intravenous administration is desired.

Topical preparations containing the active drug component can be admixed with a variety of carrier materials well known in the art, such as, e.g., alcohols, aloe vera gel, allantoin, glycerine, vitamin A and E olis, mineral oil, PPG2 myristyl propionate, and the like, to form, e.g., alcoholic solutions, topical cleansers, cleansing creams, skin gels, skin lotions, and shampoos in cream or gel formulations.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds or modulators of the present invention may also be coupled with soluble polymers as targetable drug carriers. Such polymers can include polyvinyl-pyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For oral administration, the compounds or modulators may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like.

These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds or modulators may alternatively be administered parenterally via injection of a formulation consisting of the active ingredient dissolved in an inert liquid carrier. Injection may be either intramuscular, intraluminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds or modulators is possible through the use of a liquid drench or a shampoo containing the instant compounds or modulators as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds or modulators.

The following examples illustrate the present invention without, however, limiting the same thereto.

EXAMPLE 1

Cloning of Human Sodium Channel β1A Subunit

Rapid Amplification of cDNA End (RACE-PCR): Marathon-Ready™ human adrenal gland cDNA library (Cat. No. 7430-1) was purchased from Clontech (Palo Alto, Calif.). Primary Race PCR was performed in 50 µl final volume. The reaction mixture contains 5 µl of Marathon-Ready™ human adrenal gland cDNA, 5 µl of 10× reaction buffer, 200 µM dNTP, 200 nM AP1 primer (Clontech, 5'-CCA TCC TAA TAC GAC TCA CTA TAG GGC-3' SEQ.ID.NO.:01), 200 nM human sodium channel β1 subunit specific primer SB1-10 (5'-TGG ACC TTC CGC CAG AAG GGC ACTG-3' SEQ.ID.NO.:02) and 1 µl of 50× Advatage2 DNA polymerase mixture (Clontech). The thermal cycler parameter for RACE-PCR was: initial denaturing at 94° C. for 30 sec, 5 cycles of 94° C./5 sec and 72° C./4 min, 5 cy ° C./5 sec and 70° C./4 min, and 20 cycles of 94° C./5 sec and 68° C./4 min Assessment of RACE-PCR product: The quality of the RACE-PCR reaction was assessed by testing whether the carboxyl terminus of human sodium channel $β_1$ subunit had been amplified. This was done by PCR with 1 µl of RACE-PCR product as template, and 200 nM of two human sodium channel $β_1$ subunit specific primers. The specific primers are: a forward primer SB1-11 (5'-CTG GAG GAG GAT GAG CGC TTC GAG-3' SEQ.ID.NO.:3) located at downstream of SB 1-10 and a reverse primer SB 1-13 (5'-CTA TTC GGC CAC CTG GAC GCC-3' SEQ.ID.NO.:4) located at the end of human sodium channel $β_1$ subunit. The PCR reaction parameter was: initial denaturing at 94° C. for 1 min, followed by 30 cycles of denaturing at 94° C. for 20 sec, annealing at 55° C. for 20 sec and extension at 72° C. for 1 min. As predicted, a strong 0.5-kb DNA fragment was observed, suggesting the RACE-PCR was successful in term of amplification of carboxyl terminus of human sodium channel $β_1$ subunit.

Cloning of RACE-PCR Products into pPCR-Script vector: The RACE-PCR product was cloned with PCR-Script™ Amp Cloning Kit (Statagene, Calif.) following the company provided protocol. Briefly, the RACE-PCR product was first purified by StrataPrep PCR purification column. Ten µl of purified RACE-PCR product was then blunt-ended at 72° C. for 30 min in final volume of 13 µl with 10 µl of purified RACE-PCR product, 1.3 µl of polishing buffer, 1 µl of 10 mM dNTP and 1 µl of 0.5 U/µl cloned Pfu DNA polymerase. The ligation was performed at room temperature for 1 hour in a final volume of 10 ml containing 4.5 µl of blunt-ended RACE-PCR product, 1 µl of 10 ng/µl pPCR-Script cloning vector, 1 µl of PCR-Script 10× reaction buffer, 0.5 µl of 10 mM rATP, 11 of 5 U/µl of SrfI restriction enzyme and 1 µl of 4 U/µl of T4 DNA ligase. The ligation reaction was stopped by heating the sample at 65° C. for 10 min, and finally, 2 µl of ligation mixture was transformed into XL10-Gold bacteria.

Identification of Human Sodium Channel $β_{1A}$ Clone: Since human sodium channel $β_1$ subunit specific primer was used for RACE-PCR of carboxyl terminus of $β_{1A}$ subunit, theoretically, both $β_1$ and $β_{1A}$ subunits will be cloned. To exclude $β_1$ subunit, individual clones were characterized by PCR with a pair of primers for specific amplification of $β_1$ subunit. The primers used in the PCR are: forward primer SB1-17 (5'-GTG TCT GAG ATC ATG ATG-3' SEQ.ID.NO.:5) and reverse primer SB1-13 (see above). The PCR reaction parameter was: initial denaturing at 94° C. for 1 min, followed by 30 cycles of denaturing at 94° C. for 20 sec, annealing at 55° C. for 20 sec and extension at 72° C. for 1 min. All the PCR negative clones are non-$β_1$ subunit and subjected to further sequencing analysis.

Cloning of sodium channel $β_{1A}$ subunit for human fetal brain cDNA: With human sodium channel $β_{1A}$ subunit specific primers obtained by RACE-PCR, sodium channel $β_{1A}$ was also cloned from Marathon-Ready™ human fetal brain cDNA library (Clontech cat. No. 7402-1, Palo Alto, Calif.). PCR was performed in 50 µl final volume, containing 5 µl of Marathon-Ready™ human adrenal gland cDNA, 5 µl of 10× reaction buffer, 200 µM dNTP, 200 nM SB1-6 primer (5'-GCC ATG GGG AGG CTG CTG CCC TTA GTG GTC-3' SEQ.ID.NO.:6) and SB1-19 primer (5'-GTG TGC CTG CAG CTG CTC AA-3' SEQ.ID.NO.:7) and 1 µl of 50× Advantage2 DNA polymerase mixture (Clontech). The PCR reaction parameter was: initial denaturing at 94° C. for 1 min, followed by 30 cycles of denaturing at 94° C. for 20 sec, annealing at 55° C. for 20 sec and extension at 72° C. for 1 min. Four independent clones were picked and subjected to double strained DNA sequencing analysis. All of the four independent clones from human fetal brain have identical sequences to RACE-PCR cloned $β_{1A}$ subunit from the human adrenal gland. The coding region of the human β1A nucleic acid is provided as SEQ ID NO: 12 and the entire isolated cDNA, including untranslated regions (UTR) is provided as SEQ ID NO:13. The 5'-untranslated region is the same as human voltage gated sodium channel β1 subunit. The 3' untranslated region is about 160 bp in length without the polyA tract.

Translation begins at the ATG beginning at nucleotide 4 and ends at the stop codon at nucleotide 808.

EXAMPLE 2

Primary Structure of the Human Voltage Gated Sodium Channel β1A Subunit Protein and Genomic Structure of β1 and β1A Gene (SCN1B)

By using a RACE-PCR technique, a novel human sodium channel β1A subunit was cloned. The cDNA contained an 807-base pair coding region for 268 amino acids and a 164-base pair 3'-untranslated region. The translated amino acid sequence is provided as SEQ ID NO:14 and includes a signal sequence and potential N-linked glycosylation sites as well as a transmembrane domain. The clone, designated β1A, is related to the sodium channel β1 subunit. The conserved motifs found in the sodium channel β1 subunit family include a signal peptide sequence, extracellular immunoglobulin fold domain and carboxyl terminal transmembrane domain. The predicted peptide contains hydrophobic amino-terminal residues (1-16 residues) with sequences highly predictive of the signal cleavage sites that would result in mature proteins initiating at amino acid 17 [Alanine]. The hydrophobic carboxyl terminal residues (243-262 residues) may serve as a transmembrane domain. The estimated protein molecular mass is about 28.8 kD after removing the signal peptide from the amino terminus. The cloned human sodium channel β1A subunit migrated with an apparent Mr of 32 kDa when analyzed by 8-20% SDS/PAGE. Peptide sequence comparison reveals that the predicted peptide is 72% identical to both the human sodium channel 11 subunit and the rat VGSC β1A subunit. Like the rat sodium channel β1A subunit, the human sodium channel β1A subunit contains an amino terminal region (1-149) of 100% identity to human 01 subunit and a novel carboxyl terminal region (150-268) with a less than 17% identity to that of human P1 subunit (FIG. 1). The genomic organization study of the human sodium channel β1 subunit gene, SCN1B (Makita, et al. 1994) has revealed that the gene spans about 9 kb with six exons and five introns on chromosome 19 (19q13.1-q13.2). Blast searching of human genomic sequences revealed that the amino terminal region of human sodium channel β1A subunit (1-149) are encoded by exon 1-3, while the novel carboxyl terminal region was encoded by intron 3 adjacent to exon 3 (FIG. 2). Since the site of divergence between the β1 and β1A subunits cDNA was located precisely at the exon 3-intron 3 boundary of the SCN1B gene, the human sodium channel β1A subunit should be considered as a splicing variant of the β1 subunit via the retained intron with an in-frame stop codon. However, the carboxyl terminal region of the human VGSC β1A subunit is less than 33% identical to the rat VGSC β1A subunit. Blast searching of human genomic sequence with the cDNA encoding rat β1A carboxyl terminus failed to identify any homologous region in the human β1 gene, which strongly suggests that both rat and human β1A carboxyl termini are encoded by intron 3 and the difference is due to the species differences.

Blast searching of the NIH database with the carboxyl terminal sequence of the human sodium channel β1A subunit also revealed an unassigned clone (Accession number: AI742310) in the human EST database, which was cloned from the pool of five normalized cDNA libraries. The clone AI742310 was shorter than, but 100% identical to the carboxyl terminal region (150-268 residues) of the human sodium channel $β_{1A}$. The similar blast searching failed to reveal any sequence with more than 25% identity from any other databases.

EXAMPLE 3

Generation of Polyclonal Antibodies

Two peptide sequences (HB1A-1 and HB1A-2) derived from carboxyl terminus of human β1A subunit were selected for raising polyclonal antibodies in rabbits. The amino acid sequences are: (HB1A-1) AC-RWRDRWQAVDRTGC-AMIDE (SEQ IN NO.:08) and (HB1A-2) AC-CVPHRRS-GYRTQL-AMIDE (SEQ IN NO.:09). The peptides were synthesized and antibodies were raised and purified by Bio-Source International, Inc. The antibodies were tested by ELISA against the antigen peptides and affinity purified with the same peptides. Serum and affinity purified antibodies were used for immunoanalysis, such as Western blot, immunoprecipitation, immunocytochemistry and immunohistochemistry.

EXAMPLE 4

In Vitro Translation Analysis of Human Sodium Channel β1A Subunit.

The cDNA of the human sodium channel β1A subunit was first subcloned into pAGA3 vector, which was engineered for high efficiency of in vitro transcription and translation. Briefly, the cDNA fragment encoding human sodium channel β1A subunit was excised from the pcDNA3.1 construct (See Example 6) by digested with NcoI and XbaI. An about 900 bp cDNA fragment was separated by 1% agarose gel and purified by Qiaquick Spin Purification Kit (Qiagen). The vector pAGA3 was also digested with NcoI and XbaI restriction enzymes. The purified liner vector was ligated with the cDNA fragment and transformed into bacteria. The recombinants was isolated and confirmed by restriction enzyme digestion and DNA sequencing. In vitro translation of the human sodium channel β1A subunit was done with TnT® T7 Quick Coupled Transcription/Translation System (Promega) following the vendor recommended protocol. Briefly, 1 µg hβ1A/pAGA3 construct was added to 40 µl of TNT Quick Master Mix with 2 µl of [$^{35}$S]-methionine (1000 Ci/mmmol at 10 mCi/ml) in a final volume of 50 µl. The reaction mixture was incubated at 30° C. for 90 min. Five µl of reaction mixture was mixed with an equal volume of SDS/PAGE loading buffer and subjected to 8-20% SDS/PAGE for analysis. After electrophoresis, the gel was stained with Coomassie Blue R250, dried and exposed to X-ray film. Both the human β1 and human β1A migrate to the molecular weight predicted by translation of the amino acid sequences from the corresponding nucleic acid sequences.

The in vitro translated human sodium channel β1A subunit was also analyzed by Western blot and immunoprecipitation.

EXAMPLE 5

Northern Blot Analysis of the Human β1A Sodium Channel Subunit Expression

A northern blot was used to analyze the tissue distribution of the human sodium channel β1A subunit. The cDNA fragment encoding 217-268 residues of the human sodium channel β1A was used as a probe. To make the probe, a 153 bp DNA fragment was first amplified from the DNA construct (NQC130) containing full length cDNA of human sodium channel β1A with human sodium channel β1A specific primers SB1-25 (5'-T CAA AGC ATG CCT GTC CC-3' SEQ.ID.NO.:10) and SB 1-20 (5'-TCA AAC CAC ACC CCG AGA AA-3' SEQ.ID.NO.:11). Following amplification, the PCR product was directly cloned into the pCR2.1 vector (Invitrogen) and was further confirmed by DNA sequencing. The resulting construct NQC226 was digested with the restriction enzyme HindIII and DNA was then precipitated after phenol and chloroform extraction. To label the probe, the antisense cDNA fragment was linearly amplified with Strip-EZ™ PCR kit (Ambion Tex.). The reaction was performed in 20 µl final volume, containing 25 ng linearized NQC226, 2 µl of 10× reaction buffer, 2 µl of 10× dNTP solution, 2 µl of 3000 Ci/mmol [$\alpha$-$^{32}$P]-dATP (Amersham Pharmacia Biotech), 1 U thermostable DNA polymerase and 2 µl of 10 pmo/µl of SB1-20 primer. The PCR reaction parameter was: initial denaturing at 94° C. for, 1 min, followed by 35 cycles of denaturing at 94° C. for 20 sec, annealing at 55° C. for 20 sec and extension at 72° C. for 1 min. The labeled probe was then separated from free [$\alpha$-$^{32}$P] dATP with MicroSpin™ G-50 column (Amersham Pharmacia Biotech).

Human MTN™ (Multiple Tissue Northern) blot (Cal. No. 7760-1) and Human Brain MTN™ Blot II (7755-1) were purchased from Clontech (Palo Alto, Calif.). The blots were pre-hybridized with 5 ml UltraHyb Solution (Ambion, 1×) at 42° C. for 2 hours, and then hybridized in the presence of 1×10$^6$ cpm/ml probe of human sodium channel β1A subunit at 42° C. overnight. The blots were washed with 2×200 ml of 0.2×SSC/0.1% SDS solution at 65° C. for two hours. Finally the blots were exposed to X-ray film in −80° C. freezer overnight.

2.0 kb cDNA fragment encoding human β-actin was used as the control probe. The same blots were stripped at 68° C. for 15 minutes with Strip-EZ™ removal kit provided by Ambion. The blots were then pre-hybridized with 5 ml of UltraHyb at 42° C. for 2 hour, and then hybridized in the presence of human β-actin probe for 2 hours at 42° C. The blots were washed with 2×200 ml of 0.2×SSC/0.1% SDS solution at 68° C. for two hours. Finally the blots were exposed to X-ray film in −80° C. freezer for 1 hour.

Northern blot analysis demonstrated that the VGSC β1A subunit was highly expressed in, but not limited to, most regions of human brain and skeletal muscle. Lower levels of expression were observed in heart, placenta, liver, kidney and pancrease. In brain, the VGSC β1A subunit was expressed most highly in the cerebellum region. The size of the VGSC β1A subunit transcripts varied slightly in different tissues. However, the major transcript was about 7.5 kb in size.

EXAMPLE 6

Cloning of Human β1A Sodium Channel Subunit cDNA into a Mammalian Expression Vector The cDNA of human sodium channel β1A subunit were cloned into the mammalian expression vectors pIRESneo (Clontech) and pcDNA3 (Invitrogen). The cDNA fragments encoding the human sodium channel β1A subunit were excised from pPCR-Script plasmids (NQC128) by digestion with BamHI and Not I, separated by agarose gel electrophoresis and purified by Qiaquick Spin purification kit (Qiagen). The vector pIRESneo was also linearized with BamHI and NotI and purified, and ligated with cDNA fragment of hb1A isolated from NQC128. Recombinants were isolated, and confirmed by restriction enzyme digestion and DNA sequencing. The clones NQC141 (hβ1A/pIRESneo) were then used to transfect human neuroblastoma cells (SK-N-SH) by SuperFect (Qiagen) following the vendor's protocol. Stable cell clones are selected by growth in the presence of G418. Single G418 resistant clones are isolated and shown to contain the intact Human β1A sodium channel subunit gene.

Clones containing the Human β1A sodium channel subunit cDNAs are analyzed for expression using immunological techniques, such as Western blot, immunoprecipitation, and immunofluorescence using antibodies specific to the Human β1A sodium channel subunit proteins. Antibody is obtained from rabbits inoculated with peptides that are synthesized from the amino acid sequence predicted from the Human β1A sodium channel subunit sequences. Expression is also analyzed using sodium influx assay.

The Human β1A sodium channel subunit gene was inserted into pcDNA3.1 (Invitrogen). The cDNA fragment encoding human sodium channel β1A subunit was excised from NQC130 plasmid by digested with XhoI and NotI, and the cDNA inserts isolated by agarose gel electrophoresis and purified by Qiaquick Spin Purification Kit (Qiagen). The vector, pcDNA3, was digested with BamHI and NotI, and the linear vector isolated by gel electrophoresis, and ligated with cDNA inserts. Recombinant plasmids containing human sodium channel β1A subunit were isolated, and confirmed by restriction enzyme digestion and DNA sequencing. The clone NQC139 (hβ1A/pcDNA3.1) was used to transiently transfect human neuroblastoma cells (SK-N-SH) by SuperFect (Qiagen) and the function of hb1A on modulation of sodium influx was tested by sodium influx assay.

Cells that are expressing Human sodium channel β1A subunit, stably or transiently, are used to test for expression of channel and for ligand binding activity. These cells are used to identify and examine other compounds for their ability to modulate, inhibit or activate the channel and to compete for radioactive ligand binding.

Cassettes containing the human sodium channel β1A subunit cDNA in the positive orientation with respect to the promoter are ligated into appropriate restriction sites 3' of the promoter and identified by restriction site mapping and/or sequencing. These cDNA expression vectors are introduced into fibroblastic host cells for example COS-7 (ATCC# CRL1651), and CV-1 tat [Sackevitz et al., Science 238: 1575 (1987)], 293, L (ATCC# CRL6362)] by standard methods including but not limited to electroporation, or chemical procedures (cationic liposomes, DEAE dextran, calcium phosphate). Transfected cells and cell culture supernatants can be harvested and analyzed for human sodium channel β1A subunit expression as described herein.

All of the vectors used for mammalian transient expression can be used to establish stable cell lines expressing Human β1A sodium channel subunit. Unaltered Human β1A sodium channel subunit cDNA constructs cloned into expression vectors are expected to program host cells to make Human β1A sodium channel subunit protein. In addition, Human β1A sodium channel subunit is expressed extracellularly as a secreted protein by ligating Human β1A sodium channel subunit cDNA constructs to DNA encoding the signal sequence of a secreted protein. The transfection host cells include, but are not limited to, CV-1-P [Sackevitz et al., Science 238: 1575 (1987)], tk-L [Wigler, et al. Cell 11: 223 (1977)], NS/0, and dHFr-CHO [Kaufman and Sharp, J. Mol. Biol. 159: 601, (1982)].

Co-transfection of any vector containing Human β1A sodium channel subunit cDNA with a drug selection plasmid including, but not limited to G418, aminoglycoside phosphotransferase; hygromycin, hygromycin-B phosphotransferase; APRT, xanthine-guanine phosphoribosyl-transferase, will allow for the selection of stably transfected clones. Levels of Human β1A sodium channel subunit are quantitated by the assays described herein.

Human β1A sodium channel subunit cDNA constructs are also ligated into vectors containing amplifiable drug-resistance markers for the production of mammalian cell clones synthesizing the highest possible levels of Human β1A sodium channel subunit. Following introduction of these constructs into cells, clones containing the plasmid are selected with the appropriate agent, and isolation of an over-expressing clone with a high copy number of plasmids is accomplished by selection in increasing doses of the agent.

The expression of recombinant Human β1A sodium channel subunit is achieved by transfection of full-length Human β1A sodium channel subunit cDNA into a mammalian host cell.

EXAMPLE 7

Cloning of Human β1A Sodium Channel Subunit cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculoviruses expressing Human β1A sodium channel subunit cDNA is produced by the following standard methods (InVitrogen Maxbac Manual): the Human β1A sodium channel subunit cDNA constructs are ligated into the polyhedrin gene in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA [Kitts, P. A., Nuc. Acid. Res. 18: 5667 (1990)] into Sf9 cells. Recombinant pAC360 viruses are identified by the absence of inclusion bodies in infected cells and recombinant pBlueBac viruses are identified on the basis of β-galactosidase expression (Summers, M. D. and Smith, G. E., Texas Agriculture Exp. Station Bulletin No. 1555). Following plaque purification, Human β1A sodium channel subunit expression is measured by the assays described herein.

The cDNA encoding the entire open reading frame for the Human β1A sodium channel subunit is inserted into the BamHI site of pBlueBacII. Constructs in the positive orientation are identified by sequence analysis and used to transfect Sf9 cells in the presence of linear AcNPV mild type DNA.

Authentic, active Human β1A sodium channel subunit is found in the cytoplasm of infected cells. Active Human β1A sodium channel subunit is extracted from infected cells by hypotonic or detergent lysis.

EXAMPLE 8

Cloning of Human β1A Sodium Channel Subunit cDNA into a Yeast Expression Vector

Recombinant Human β1A sodium channel subunit is produced in the yeast S. cerevisiae following the insertion of the optimal Human β1A sodium channel subunit cDNA cistron into expression vectors designed to direct the intracellular or extracellular expression of heterologous proteins. In the case of intracellular expression, vectors such as EmBLyex4 or the like are ligated to the Human β1A sodium channel subunit cistron [Rinas, U. et al., Biotechnology 8: 543-545 (1990); Horowitz B. et al., J. Biol. Chem. 265: 4189-4192 (1989)]. For extracellular expression, the Human β1A sodium channel subunit cistron is ligated into yeast expression vectors which fuse a secretion signal (a yeast or mammalian peptide) to the $NH_2$ terminus of the Human β1A sodium channel subunit protein [Jacobson, M. A., Gene 85: 511-516 (1989); Riett L. and Bellon N. Biochem. 28: 2941-2949 (1989)].

These vectors include, but are not limited to pAVE1>6, which fuses the human serum albumin signal to the expressed cDNA [Steep O. Biotechnology 8: 42-46 (1990)], and the vector pL8PL which fuses the human lysozyme signal to the expressed cDNA [Yamamoto, Y., Biochem. 28: 2728-2732)]. In addition, Human β1A sodium channel subunit is expressed in yeast as a fusion protein conjugated to ubiquitin utilizing the vector pVEP [Ecker, D. J., J. Biol. Chem. 264: 7715-7719 (1989), Sabin, E. A., Biotechnology 7: 705-709 (1989), McDonnell D. P., Mol. Cell Biol. 9: 5517-5523 (1989)]. The levels of expressed Human β1A sodium channel subunit are determined by the assays described herein.

EXAMPLE 9

Purification of Recombinant Human β1A Sodium Channel Subunit

Recombinantly produced Human β1A sodium channel subunit may be purified by antibody affinity chromatography.

Human β1A sodium channel subunit antibody affinity columns are made by adding the anti-human β1A sodium channel subunit antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1 M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized Human β1A sodium channel subunit are slowly passed through the column. The column is then washed with phosphate-buffered saline together with detergents until the optical density (A280) falls to background, then the protein is eluted with 0.23 M glycine-HCl (pH 2.6) together with detergents. The purified Human β1A sodium channel subunit protein is then dialyzed against phosphate buffered saline.

EXAMPLE 10

Immunohistochemistry of Human Tissue

Immunohistochemistry: Protocols for immunohistochemistry have been previously described (D'Andrea, et al, 1998). All incubations were performed at room temperature. After microwaving the slides in Target (Dako, Carpenturia, Calif.), the slides were placed in PBS, then 3% $H_2O_2$, rinsed in PBS and then appropriate blocking serum was added for 10 minutes. Subsequently, primary antibody, either rabbit polyclonal anti-human hβ1A antibody (HB1A-1, see Example 3) at a titer of 1:200 or rabbit polyclonal anti-rat β1A antibody at a titer of 1:400 was applied to the slides for 30 minutes. Proper species isotype antibody (Vector Labs, Burlingham, Calif.) was substituted as the primary antibody for the negative control. After several PBS washes, a biotinylated secondary antibody (Vector Labs) was placed on the slides for 30 minutes. Subsequently, the slides were washed in PBS and then the avidin-biotin complex (ABC, Vector Labs) was applied to the cells for 30 minutes. The presence of the primary antibodies was detected by adding DAB (3'-diaminobenzidine HCl;

Biomeda, Foster City, Calif.) for 2 times 5 minutes. Slides were briefly exposed to Mayer's hematoxylin for 1 minute, dehydrated and coverslipped.

Results:

With anti-human β1A antibody: We were able to detect intracellular β1A in the human DRG neurons. We also localized membrane-associated β1A in the neuronal fibers of the DRG as well. We also screened a myriad of human tissues and determine the β1A protein to be present in the epithelial cells of the gut (brush boarder), of the collecting tubules (distal>proximal) of the kidney (demonstrating prominent labeling), and prostate. We also observed β1A immunolabeling in the brain (cortex pyramidal neurons, cerebellar Purkinje cells, and many of the neuronal fibers throughout the brain), in the endothelial cells of the lung and other tissues, membrane of macrophages in the lung and uterus, and in the cardiocytes of the heart. We did not observe significant, detectable levels of β1A in the following tissues: thyroid, spleen, liver, and pancreas. We also observed similar distribution of β1A in rat tissue with this anti-human b1a antibody.

EXAMPLE 11

Patch Clamp Analysis of VGSC β1A Subunit Expressed in *Xenopus* Oocytes

1. In vitro synthesis of cRNA: The expression constructs of the β1A and $Na_V1.2$ (a type II alpha subunit of the voltage gated calcium channel protein family obtained from Dr. A. Correa, UCLA Medical Center, Department of Anesthesiology) were linearized with restriction enzymes. The cRNAs were synthesized in vitro with T7 RNA polymerase using reagents and protocols of the mMESSAGE mMACHINE™ transcription kit (Ambion, Austin, Tex.), with the exception that the LiCl precipitation step was repeated twice. The cRNAs were suspended in diethylpyrocarbonate (DEPC)-treated $H_2O$ at a final concentration of 1-2 mg/ml.

2. Oocyte Isolation: Frogs (*Xenopus laevis*) were anesthetized by immersion into 0.15-0.17% tricaine in water and removed from the tricaine bath. Ovarian lobes were then exposed through a small incision made into their abdominal wall, removed and placed into sterilized $Ca^{2+}$-free OR-2 solution ($Ca^{2+}$-free OR-2: 82.5 mM NaCl, 2.5 mM KCl, 1 mM $MgCl_2$ and 5 mM HEPES, pH adjusted to 7.6 with NaOH) and the frogs returned to tricaine-free water for recovery. The ovarian lobes were then rinsed with sterile water, teased open, and incubated at room temperature in $Ca^{2+}$-free OR-2 containing 2 mg/ml collagenase (type I, BRL) to cause release and defolliculation of oocytes. After 1 hr on an orbital shaker (ca 60 cycles per min) the oocytes were transferred to a Petri dish with OR-2. Dead and too small oocytes were removed by aspiration and the selected oocytes were washed several times with collagenase free and $Ca^{2+}$-free OR-2 solution, incubated under agitation for an additional hour with solution changes every 7-8 min, and placed into an incubator at 19° C. and incubated for an additional 1 hr in a 1:4 mixture of sterile SOS and $Ca^{2+}$-free OR-2 solutions (SOS: 100 mM NaCl, 2 mM KCl, 1.8 mM $CaCl_2$, 1 mM $MgCl_2$, 5 mM HEPES, pH adjusted to 7.6 with NaOH) and 30 min in 1:3 SOS/$Ca^{2+}$-free OR-2. The oocytes were then placed into 100% SOS, sorted once more and kept at 19° C.

3. Injections: Oocytes were injected with 50 nl containing the cRNAs to be translated at a final concentration of 100 μg/ml of each species, and oligonucleotides at the indicated concentrations. Injections were performed immediately after isolation or at varying times thereafter for up to three days.

Injected oocytes were kept at 17-19° C. in sterile SOS containing 50 μg/ml gentamycin with daily solution changes until used for electrophysiological testing (4-6 days post-injection).

4. Electrophysiological recordings from oocytes: The cut-open vaseline gap voltage clamp of oocyte (Taglialatela et al., 1992) was performed with a CA-1 cut open oocyte clamp setup (Dagan, Minneapolis, Minn.). The experimental external solution contained 120 mM NMG-Mes, 10 mM HEPES, and 2 mM $Ca(Mes)_2$ at pH 7.4. The experimental internal solution contained 120 mM NMG-Mes, 10 mM HEPES, and 2 mM EGTA at pH 7.4. Leakage and linear capacity currents were compensated and subtracted on-line using p/–4 protocol from –90 mV holding potential (SHP).

Signals were filtered with an eight pole Bessel filter to ⅕ of the sampling frequency. All the recordings were performed at room temperature (22-23° C.).

5. Data Acquisition and Analysis: Gating and ionic currents were acquired with a PC44 board (Innovative Technologies, Moorpark, Calif.), which interfaces with a Pentium-based computer via an IBM-compatible AT slot.

The peak G-V curve was obtained with an internal solution of 15 mM NaMes and an external solution of 1 mM NaMes (with N-methyl-glucamine (NMG) to replace the remaining cations). The reversal potential was determined from an instantaneous I-V after subtracting the gating component, and peak conductance was calculated by dividing peak current by the voltage difference from the reversal potential. Within the time resolution of the clamp, the instantaneous I-V curve was linear, so no further corrections were made.

Figure 3:
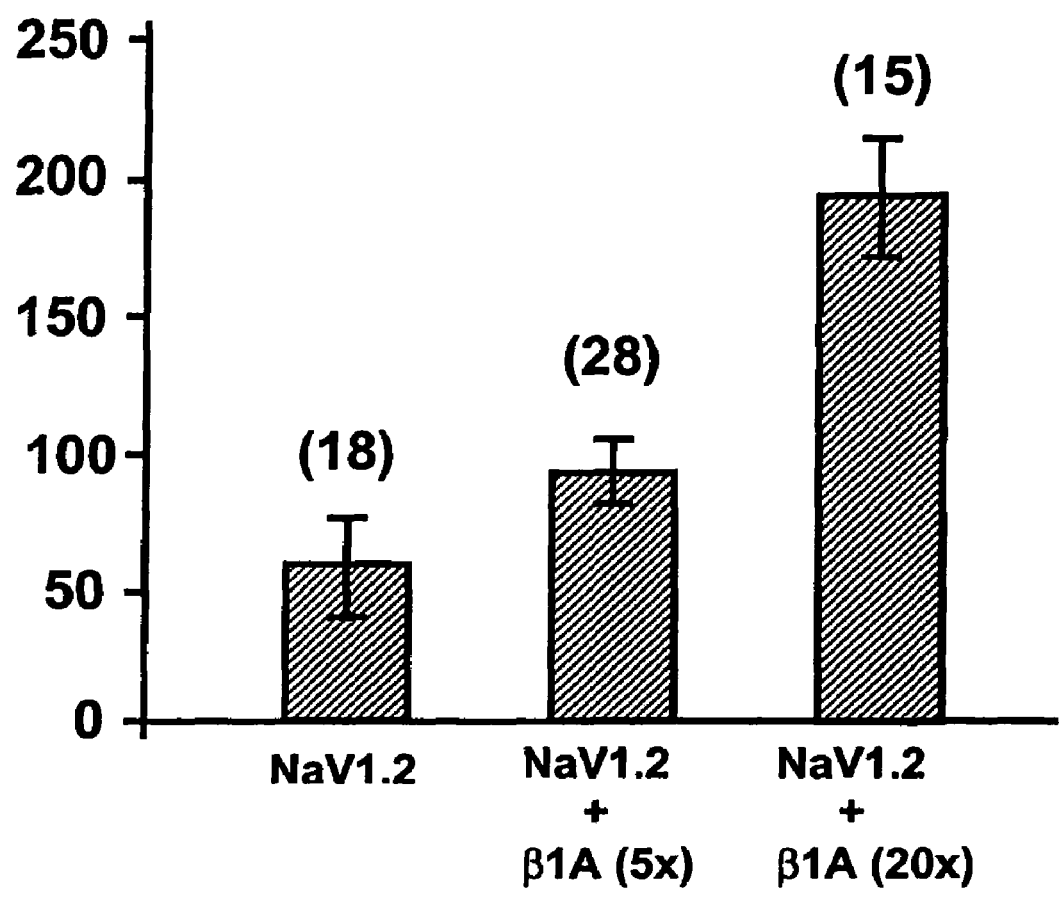
FIG. 3 demonstrates co-expression of the β1A and the $Na_v1.2$ subunits in *Xenopus* oocyte. Peak ionic current conducted by $Na_v1.2$ was dose-dependently increased by its coexpression with the β1A subunit in oocytes. The cRNAs ratio of $Na_v1.2$ and the β1A subunits are indicated at the bottom of the bars. The data were averaged from the number of oocytes shown on the top of the bars. The error bars represent the SEM.

6. Results: As shown in FIG. 3, the ionic current conducted by $Na_V1.2$ was increased significantly by coexpression with the β1A subunit in oocytes. At the cRNA ratio of 1:20 ($Na_V1.2$ vs β1A), the ionic current was increased about 3 fold. The results indicate that the β1A subunit plays an important role in increasing the number of the functional sodium channels present on the cell surface.

EXAMPLE 12

Up-Regulation and Redistribution of β1A Subunit in Rat Dorsal Root Ganglia Neurons Following Spinal Nerve Ligation 1. Spinal Nerve Ligation. All procedures involving the use of animals were carried out in accordance with the guidelines of the Institutional Animal Care and Use Committee, The R.W. Johnson Pharmaceutical Research Institute and American Association for Laboratory Animal Care. Spinal nerve ligation (SNL) was performed as described by Kim and Chung (1992). Briefly, male Sprague-Dawley rats (Harlan, Indianapolis, Ind.) weighing approximately 200 g were anesthetized with isoflurane. The spinal nerve at the level of L5 or L6 was exposed through an incision left of the dorsal midline and, following removal of the left L6 transverse vertebral process, tightly ligated with 6-0 silk. The incision was then closed with 4.0 vicryl (fascia) and skin clips. Animals were allowed to recover from anesthesia and were assessed for hind limb motor function prior to being returned to group housing. Naive animals did not undergo surgery.

2. Evaluation of Mechanical Allodynia. Allodynia was assessed by placing rats individually on a wire mesh platform such that the plantar surface of each hind paw could be stimulated from below. An ascending series of tactile stimuli was applied using calibrated von Frey filaments (0.25-15 g) until a rapid paw lift response was observed. An "up-down" method (Chaplan et al., 1994) was employed to determine the response threshold in grams. Animals from which tissue was obtained were tested at several time points post-surgically to assure that response thresholds of the ipsilateral paw were at or below the 4 g criterion. Additionally, a separate age matched group of animals (n=3-12 ligated, n=7 naive) was tested for mechanical allodynia at various times (3 d, 10 d, 21 d, and 8 wk) following surgery to profile the time course of ipsilateral and contralateral response thresholds, as well as the response of naive animals.

3. Tissue Preparation. At 2 d, 14 d and 8 wk after surgery, animals (n=3-5) were sacrificed by $CO_2$ asphyxiation and transcardially perfused with 4% paraformaldehyde. The L4 and L5 DRGs were removed, processed for paraffin embedding in a multi-tissue format, serially sectioned at 5 μm and mounted onto Superfrost-Plus slides (Fisher, Pittsburgh, Pa.).

4. Immunohistochemistry. Protocols for routine immunohistochemistry (IHC) have been previously described (D'Andrea et al., 1998). Briefly, paraffin slides were dewaxed, hydrated and microwaved in Target buffer (Dako, Carpenteria, Calif.). Sections were cooled, placed in phosphate-buffered saline (PBS, pH 7.4) and then treated with 3.0% $H_2O_2$ for 10 min to inactivate endogenous peroxidases. All subsequent reagent incubations and washes were performed at room temperature. Normal blocking serum (Vector Labs, Burlingame, Calif.) was placed on the tissues for 10 min followed by brief rinsing in PBS. Tissues were then incubated with primary antibody for 30 min, and washed, and then treated with biotinylated secondary antibodies, goat anti-rabbit (Vector Labs) for 30 min. Previously characterized (Kazen-Gillespie et al., 2000) rabbit polyclonal anti-β1A and anti-β1 antibodies were used at titers of 1:400. Following a rinse in PBS, tissues were treated with the avidin-biotin-HRP complex reagent (Vector Labs) for 30 min. Slides were treated 2×5 minutes with 3,3'-diaminobenzidine (DAB, Biomeda, Foster City, Calif.), rinsed, counterstained with hematoxylin, dehydrated, cleared in xylene and coverslipped. Monoclonal antibodies specific to neuron-specific nuclear protein (NeuN, 1:1,000; Chemicon, Temecula, Calif.) were used as a positive control to confirm tissue antigenicity and reagent quality. Negative controls included replacement of the primary antibody with species IgG isotype non-immunized serum (Vector Labs).

5. Evaluation of β1A and β1 immunolabeling. Tissues mounted on slides in a multi-tissue format were stained simultaneously to minimize potential staining variability. Ipsilateral and contralateral DRG neurons with prominent nuclei from the L4 and L5 from each animal were characterized as nociceptive if the diameter was <25 μm in diameter; all others were designated as sensory neurons (Oh et al., 1996; Gould et al., 1998). The staining of 30-40 neurons per DRG per animal was scored according to the following criteria: 1) no immunoreactivity was scored as 0.0; 2) weak immunoreactivity was scored as 1.0; 3) moderate immunoreactivity was scored as 2.0, and 4) intense immunoreactivity was scored as 3.0. If the immunolabeling intensity was between these whole numbered units, a 0.5 increment was used (i.e. 1.5 weak to moderate labeling). These data were then averaged per animal and per group (n=3-5 per group).

The morphology of the β1A and β1 immunoreactivity in the L5 nociceptive and sensory DRG neurons were also characterized as 1) homogeneous: a diffuse labeling pattern; 2) punctate: several clumpy, intracellular, Nissl-like aggregates of staining; and 3) membrane: prominent peripheral labeling located predominantly along the cell membrane. Data are presented as a percentage of each labeling pattern observed per DRG per group (Table 2).

Data and Statistical Analysis. The β1A and β1 staining data were grouped to identify the spinal level of the DRG (L4 or L5), laterality (contralateral or ipsilateral), neuronal type (small or large), and ligation time (naive, 2 days, 14 days, and 8 weeks post-SNL). Within the resulting 16 subgroups, both protein staining intensity measures and ligation time factors represented naturally ordered values. Initial data evaluation indicated the absence of normality in the distribution of the scored response, suggesting modeling by a nonparametric method. Thus a one-sided Jonckheere-Terpstra test was chosen to evaluate the basic hypothesis that the distribution of mean protein expression scores changed across ligation time.

Results: Mechanical allodynia: SNL rats exhibited a dramatic ipsilateral decrease in Von Frey response threshold to less than 2 g and then 1 g by three and ten days post lesion, respectively. This enhanced level of tactile sensitivity in the ipsilateral paw was retained throughout the eight week test period. Contralateral paw response thresholds were in general similar to naive or prelesion responses, i.e., 13-15 g; however, enhanced sensitivities (8-10 g) were seen at three days post-lesion, possibly reflecting a generalized post-surgical effect. Naive animal responses to Von Frey stimulation were within the 13-15 g range over the entire eight-week period, bilaterally.

Intensity of β1A labeling in DRG. A graphic presentation of the mean staining intensities in each group of DRGs studied is shown in FIG. 4. In both nociceptive and sensory neurons, β1A immunolabeling increased with post-surgical time, this increase being most prominent in the ipsilateral neurons. Table 1 lists the p values resulting from Jonckheere-Terpstra analysis of the intensity versus time relationship. Intensity of β1 labeling in DRG. A graphic presentation of the mean labeling intensity for each group of DRGs studied is presented in FIG. 5. Although β1 immunolabeling tended to increase with post-surgical time, this trend was of greater significance in the L4 than the L5 DRG (Table 1).

Subcellular distribution of β1A and β1 immunoreactivity. In naive rats, the sodium channel β1A and β1 subunits exhibited identical subcellular localizations, virtually all of the staining being diffusely distributed throughout the cell. Post-SNL, however, the subcellular distributions of the subunits diverged markedly. Whereas staining for the β1 subunit remained uniformly distributed within the DRG neurons in which it was located, β1A localization, most notably in the nociceptive neurons, assumed an altered pattern of distribution post SNL; staining for the β1A subunit became discreetly localized in an area proximal to the cell membrane. Whereas virtually 100% of β1A staining was diffusely distributed in DRG cells from naive rats, only 23% was homogeneously distributed in nociceptive, ipsilateral, L5, DRG neurons (Table 2). In these cells, 51% of the staining for β1A was localized proximal to the cell membrane. Ipsilateral sensory DRG neurons, as well as both nociceptive and sensory contralateral neurons, also exhibited altered subcellular β1A distributions. In these cells, 58-76% of β1A staining remained diffuse, about 20% appeared punctate or Nissl-like, and the remainder was located adjacent to the cell membrane (Table 2). Thus, in addition to exhibiting differences in the intensity of their labeling in DRG neurons post-SNL, sodium channel β1A and β1 subunits differed markedly in their post-SNL subcellular localizations.

EXAMPLE 13

Screening and Identification of Small Molecules that Interact Directly with VGSC β1A Subunit One of the regulatory functions of the β1A subunit is to increase functional channels by recruitment of α subunits to the cell surface. Disruption of the normal function of the $β_{1A}$ subunit may result in down regulation of functional sodium channel in DRG after nerve injury. Small molecules that interact with the β1A subunit are identified by CETEK capillary zone electrophoresis technology. First, the target protein, VGSC $β_{1A}$ subunit was over-expressed in bacteria. The cDNA of the β1A subunit was subcloned into pET29b bacteria expression vector (Novagen). The expression construct was then transformed into *E. Coli* BL21 (DE3) and the expression of the β1A induced by adding IPTG at room temperature for 4 hours. A single fresh colony from a plate was inoculated into 50 ml LB medium containing 15 μg/ml of Kanamycin, and incubated with shaking at 37° C. until the $OD_{600}$ reached 0.6. The expression of β1A subunit fusion protein was induced by adding IPTG to final concentration to 1 mM and incubated at room temperature for 4 hours. For SDS-PAGA analysis, 100 μl of cultures before and after IPTG induction were aliquoted. The cells were spun down, resuspended in 20 ml of SDS loading buffer and subjected to 4-20% SDS-PAGE. After electrophoresis, the gel was stained by SimpleBlue™ SafeStain (Invitrogen) and destained overnight with water. Lane 1: high molecular weight protein marker (Bio-Rad), lane 2, total cell lysate before induction, and lane 3 total cell lysate after induction.

The resulting fusion protein of the β1A subunit had an S-tag, a 15 amino acid motif, at its N-terminus and six histidines at its C-terminus. The fusion protein is then affinity purified with a $Ni^+$ column, and non-covalently labeled with a fluorophore at the S-tag. The mobility shifts of the $β_{1A}$ subunit in capillary electrophoresis after binding with a small molecule that changes the conformation or surface charge of the target protein is detected with a laser-induced fluorescence.

EXAMPLE 14

Sodium Channel Functional Assay:

The regulatory activity of the β1A subunit is also studied by its co-expression with the pore-forming and ion-conducting α subunit in eukaryotic cells, where sodium channel activity is tested by functional bioassays. The α subunits are, but not limited to, $Na_V1.2$, $Na_V1.3$, $Na_V1.6$, $Na_V1.8$ and $Na_V1.9$, respectively. Determination of sodium channel activity is performed by using two cell-based assays. The first assay involves culturing cells in 96-well plates containing a scintillating base plate. The cell monolayers are stimulated with veratridine or any other appropriate sodium channel activator in the presence of [$^{14}C$]-guanidine. When the sodium channel is open, the [$^{14}C$]-guanidinium ions flow down their concentration gradient into the cells. Since the cells are in close proximity to the scintillating base, light is emitted. The amount of light emitted is proportional to the level of sodium channel activity and is quantitated using a scintillation counter. The second assay utilizes a fluorescent, potential-sensitive dye. Monolayers of cells are loaded with the potential-sensitive dye for 30 min at 37° C. After this incubation period, the cells are stimulated with veratridine or any other sodium channel activator, and the change in fluorescence is monitored by either a fluorimeter, fluorescent imaging plate reader (FLIPR) or by a fluorimeter-based cell imaging system. When the cells depolarize, the dye associates with cell membrane, resulting in increased fluorescence. When the cells hyperpolarize, the dye disassociates from the membrane, resulting in decreased fluorescence.

EXAMPLE 15

Cell Adhesion Assay:

Because the sodium channel β subunits have been implicated in homophilic cell-cell adhesion, the cell adhesion function of the β1A subunit is tested. The adhesion assay utilizes L cell mouse fibroblasts, which lack most of the macromolecules required for cell-cell adhesion. These L cells are stably or transiently transfected with β1A and plated in 96-well plates. Another set of L cell-β1A transfectants are loaded with a viable fluorescent dye and added to the cultures in the 96 well plates in the presence or absence of candidate compounds. After a determined incubation period, the plates are placed in a fluorescence plate reader. If homophilic cell-cell adhesion has occurred, a detectable increase in fluorescence is observed. To determine specific activity, the signal is compared to the fluorescence observed using untransfected L cells labeled with viable fluorescent dye.

TABLE 1

Statistical analyses of trends over time post-SNL in the level of β1A and β1 expression in DRG neurons. The p values given were obtained with one-tailed, Jonckheere-Terpstra analyses of the data underlying FIGS. 9 and 10.

| | Side Relative | | p value | |
| --- | --- | --- | --- | --- |
| DRG | to Ligation | DRG Neuron Type | β1A | β1 |
| L5 | ipsilateral | nociceptive | 0.003* | 0.058 |
| | | sensory | 0.011* | 0.058 |
| | contralateral | nociceptive | 0.029* | 0.042* |
| | | sensory | 0.035* | 0.097 |
| L4 | ipsilateral | nociceptive | 0.007* | 0.023* |
| | | sensory | 0.006* | 0.001* |
| | contralateral | nociceptive | 0.001* | 0.041* |
| | | sensory | 0.036* | 0.019* |

*p value < 0.05

TABLE 2

Subcellular distribution of β1A and β1 staining in L5 DRG neurons two weeks post-SNL.

| | Side Relative | Staining | Percent of Total | |
| --- | --- | --- | --- | --- |
| Antibody | to Ligation | Distribution | Nociceptive | Sensory |
| β1A | Ipsilateral | Membrane | 51 | 11 |
| | | Punctate | 26 | 18 |
| | | Homogeneous | 23 | 71 |
| | Contralateral | Membrane | 28 | 4 |
| | | Punctate | 14 | 20 |
| | | Homogeneous | 58 | 76 |
| β1 | Ipsilateral | Membrane | 0 | 0 |
| | | Punctate | 0 | 0 |
| | | Homogeneous | 100 | 100 |
| | Contralateral | Membrane | 0 | 0 |
| | | Punctate | 0 | 0 |
| | | Homogeneous | 100 | 100 |

REFERENCES

Balser J R (1999) "Structure and function of the cardiac sodium channels" *Cardiovasc Res.* 42: 327-38.

Catterall W A (1992) Cellular and molecular biology of voltage-gated sodium channels. Physiol Rev 72:S15-S48.

Catterall W A (1993) Structure and function of voltage-gated ion channels. Trends Neurosci 16:500-506.

Chabal C, Russel L C, Burchiel K J (1989) The effect of intravenous lidocaine, tocainide, and mexiletine on spontaneously active fibers originating in rat sciatic neuromas. Pain 38:333-338.

Chaplan S R, Bach F W, Pogrel J W, L L J M, Yaksh T L. Quantitative assessment of tactile allodynia in the rat paw. J Neurosci Meth 1994; 53:55-63.

D'Andrea M R, Derian C K, Letureq D, Baker S M, Brunmark A, Ling P, Darrow A L, Santulli R J, Brass L F, Andrade-Gordon P. Characterization of protease activated receptor (PAR-2) immunoreactivity in normal human tissues. J. Histochem. Cytochem. 1998; 46:157-164.

Devor M, Keller C H, Deerinck T J, Ellisman M H. (1989) Na+ channel accumulation on axolemma of afferent endings in nerve end neuromas in Apteronotus. Neurosci Lett 102:149-154.

Devor M, Wall P D, Catalan N (1992) Systematic lidocaine silences ectopic neuroma and DRG discharge without blocking nerve conduction. Pain 48:261-268.

Devor M (1994) The pathophysiology of damaged peripheral nerves. In Texbook of Pain, eds. Wall P D, Melzack R. (Churchill Liningstone, Edinburgh), $2^{nd}$ Ed., pp. 79-101.

Dib-Hajj S, Black J A, Felts P, Waxman S G (1996) Downregulation of transcripts for Na channel α-SNS in spinal sensory neurons following axotomy. PNAS 93:14950-14954.

England J D, Gamboni F, Ferguson M A, Levinson S R (1994) Sodium channels accumulate at the tips of injured axons. Muscle Nerve 17:593-598.

England J D, Happel L T, Kline D G, Gamboni F, Thouron C L, Liu Z P, Levinson S R (1996) Sodium channel accumulation in humans with painful neuromas. Neurology 4:272-276.

Gould H J $3^{rd}$, England J D, Liu Z P, Levinson S R. Rapid sodium channel augmentation in response to inflammation induced by complete Freund's adjuvant. Brain Research 1998; 802:69-74.

Isom L L, De Jongh K S, Patton D E, Reber B F X, Offord J, Charbonneau H, Walsh K. Goldin A L and Catterall W A (1992) Primary Structural and Functional Expression of the β1 Subunit of the Rat Brain Sodium Channel" Science, 256; 839-842.

Isom L L, De Jongh K S, Catterall W A (1994) Auxiliary β subunits of voltage-gated ion channels. Neuron 12:1183-1194.

Isom L L, Ragsdale D S, De Jongh K S, Westenbroek R E, Reber B F X, Scheuer T, Catterall W A (1995) Structure and function of the β2 subunit of brain sodium channels, a transmembrane glycoprotein with a CAM motif. Cell 83:433-442.

Isom L L, Catterall W A (1996) "Na+ channel subunits and Ig domains" *Nature;* 383(6598): 307-8.

Kazen-Gillespie K, Ragsdale D S, D'Andrea M R, Laura N. Mattei, Rogers K E, Isom L L (2000) Cloning, localization, and functional expression of sodium channel β1α subunits. J Biol. Chem 275:2:1079-1088.

Kazen-Gillespie K, Ragsdale D S, D'Andrea M R, Rogers K E, Isom L L. Cloning, localization, and functional expression of sodium channel β1A subunits. J Biol Chem 2000; 275:1-12.

Kim S H, Chung J M (1992) An experimental model for peripheral neuropathy produced by segmental spinal nerve ligation in the rat. Pain 50:355-363.

Kim S H, Chung J M. An experimental model for peripheral neuropathy produced by segmental spinal nerve ligation in the rat. Pain 1992; 50:355-363.

Marban E, Yamagishi T, Tomaselli G F *J Physiol (Lond)* (1998) "Structure and function of voltage-gated sodium channels" 508 (Pt 3):647-57.

Matzner O, Devor M (1992) $Na^+$ conductance and the threshold for repetitive neuronal firing. Brain Res 597:92-98.

Matzner O, Devor M (1994) Hyperexcitability at sites of nerve injury depends on voltage-sensitive Na+ channels. J Neurophysiol 72:349-359.

Sutkowski E M and Catterall W A (1990) "β1 subunits of sodium channels" J. Biol. Chem. 265; 12393-12399.

Nordin M, Nystrom B, Wallin U, Hagbarth K-E (1984) Ectopic sensory discharges and paresthesiae in patients with disorders of peripheral nerves, dorsal roots and dorsal columns. Pain 20:231-245.

Ochoa J, Torebjork H E (1980) Paresthesiae from ectopic impulse generation in human sensory nerves. Brain 103: 835-854.

Oh Y, Sashihara S, Black J A, Waxman S G. $Na^+$ channel β1 subunit mRNA: differential expression in rat spinal sensory neurons. Mol Brain Res 1995; 30:357-361.

Omana-Zapata I, Khabbaz M A, Hunter J C, Clarke D E, Bley K R (1997) Tetrodotoxin inhibits neuropathic ectopic activity in neuromas, dorsal root ganglia and dorsal horn neurons. Pain 72(1-2):41-9.

Porreca F, Lai J, Bian D, Wegert S, Ossipov M H, Eglen R M, Kassotakis L, Novakovic S, Rabert D K, Sangameswaran L, Hunter J C (1999) "A comparison of the potential role of the tetrodotoxin-insensitive sodium channels, PN3/SNS and NaN/SNS2, in rat models of chronic pain" Proc Natl Acad Sci USA; 96: 7640-4.

Rizzo M A (1997) Successful treatment of painful mononeuropathy with carbamazepine: insights into a possible molecular pain mechanism. J Neurol Sci 152:103-106.

Tanaka M, Cummins T R, Ishikawa K, Dib-Hajj S D, Black J A, Waxman S G (1998) SNS Na+ channel expression increases in dorsal root ganglion neurons in the carrageenan inflammatory pain model. NeuroReport 9(6):967-72.

Wallace R H, Wang D W, Singh R, Scheffer I E, George A L Jr, Phillips H A, Saar K, Reis A, Johnson E W, Sutherland G R, Berkovic S F, Mulley J C (1998) "Febrile seizures and generalized epilepsy associated with a mutation in the Na+-channel beta1 subunit gene SCN1B" *Nature Genetics;* 19: 366-70.

Waxman S G, Brill M H (1978) Conduction through demylineated plaques in multiple sclerosis: computer simulations of facilitation by short internodes. J Neurol Neurosurg 41:408-417.

Waxman S G, Kocsis J D, Black J A (1994) Type III sodium channel mRNA is expressed in embryonic but not adult spinal sensory neurons, and is reexpressed following axotomy. J Neurophysiol 72:466-470.

Woolf C J, Safieh-Garabedian B, Ma Q-P, Crilly P, Winters J (1994) Nerve growth factor contributes to the generation of inflammatory sensory hypersensitivity. Neuroscience 62:327-331.

Waxman S G, Dib-Hajj S, Cummins T R, Black J A. Sodium channels and pain. PNAS 1999; 96(14):7635-9.

SEQUENCE LISTING

<110> Qin, Ning
  Codd, Ellen
  D'Andrea, Michael
<120> DNAs encoding human betala sodium channel subunit
<130> ORT-1221
<140>
<141>
<160> 14
<170> PatentIn Ver. 2.1
<210> 1
<211> 27
<212> DNA
<213> Artificial Sequence
<220>
<223> Description of Artificial Sequence: oligonucleotide primer
<400> 1
ccatcctaat acgactcact atagggc
<210> 2
<211> 25
<212> DNA
<213> Artificial Sequence
<220>
<223> Description of Artificial Sequence: oligonucleotide primer
<400> 2
tggaccttcc gccagaaggg cactg
<210> 3
<211> 24
<212> DNA
<213> Artificial Sequence
<220>
<223> Description of Artificial Sequence: oligonucleotide primer
<400> 3
ctggaggagg atgagcgctt cgag
<210> 4
<211> 21
<212> DNA
<213> Artificial Sequence
<220>
<223> Description of Artificial Sequence: oligonucleotide primer
<400> 4
  ctattcggcc acctggacgc c
<210> 5
<211> 18
<212> DNA
<213> Artificial Sequence
<220>
<223> Description of Artificial Sequence: oligonucleotide primer
<400> 5
gtgtctgaga tcatgatg
<210> 6
<211> 30
<212> DNA
<213> Artificial Sequence
<220>
<223> Description of Artificial Sequence: oligonucleotide primer
<400> 6
gccatgggga ggctgctggc cttagtggtc
<210> 7
<211> 20
<212> DNA
<213> Artificial Sequence
<220>
<223> Description of Artificial Sequence: oligonucleotide primer
<400> 7
gtgtgcctgc agctgctcaa
<210> 8
<211> 14
<212> PRT
<213> Artificial Sequence
<220>
<223> Description of Artificial Sequence: synthetic peptide
<400> 8
Arg Trp Arg Asp Arg Trp Gln Ala Val Asp Arg Thr Gly Cys
1               5                   10
<210> 9
<211> 13
<212> PRT
<213> Artificial Sequence
<220>
<223> Description of Artificial Sequence: synthetic peptide
<400> 9
Cys Val Pro His Arg Arg Ser Gly Tyr Arg Thr Gln Leu
1               5                   10
<210> 10
<211> 18
<212> DNA
<213> Artificial Sequence
<220>
<223> Description of Artificial Sequence: oligonucleotide primers for Northern blot analysis
<400> 10
tcaaagcatg cctgtccc
<210> 11
<211> 19
<212> DNA
<213 Artificial Sequence
<220>
<223> Description of Artificial Sequence: oligonucleotide primers for Northern blot analysis
<400> 11
tcaaaccaca ccccggaaa
<210> 12
<211> 807
<212> DNA
<213> *Homo sapiens*
<400> 12
atggggaggc tgctggcctt agtggtcggc gcggcactgg tgtcctcagc
  ctgcgggggc 60
tgcgtggagg tggactcgga gaccgaggcc gtgtatggga tgaccttcaa aat-
  tctttgc 120
atctcctgca agcgccgcag cgagaccaac gctgagacct tcaccgagtg
  gaccttccgc 180
cagaagggca ct-gaggagtt tgtcaagatc ctgcgctatg agaatgaggt
  gttgcagctg 240
gaggaggatg agcgcttcga gggccgcgtg gtgtggaatg gcagccgggg
  caccaaagac 300 ctgcaggatc tgtctatctt catcaccaat gtcacctaca accactcggg cgactacgag 360
tgccacgtct accgctgct cttcttcgaa aactacgagc acaacaccag cgtcgtcaag 420
aagatccaca ttgaggtagt ggacaaaggt gagtcgggtg ctgcctgccc ctttaccgtc 480
acccaccgga gagccagatg gagggacaga tggcaggcag tggacaggac aggctggctc 540
tgtgcctggc cagccaaccc cccacagcag cgggctgagg gggaggggag cagcccctcc 600
tgcccactcc agctctggcc tctgtttctc tccagcccac ggagaggtca aag, catgcct 660
gtcccccaca gacgctccgg gtacagaacc cagctctgtc acctgtgctg tatgacctct 720
ggcaggtgcc ttctgtctct gagccaaagg gttgtcctgg gcttgcccgg gataataatc 780
cgatgtgttt ctcggggtgt ggtttga 807

<210> 13
<211> 974
<212> DNA
<213> Homo sapiens
<400> 13
gccatgggga ggctgctggc cttagtggtc ggcgcggcac tggtgtcctc agcctgcggg 60
ggctgcgtgg aggtggactc ggagaccgag gccgtgtatg ggatgacctt caaaattctt 120
tgcatctcct gcaagcgccg cagcgagacc aacgctgaga ccttcaccga gtggaccttc 180
cgccagaagg gcactgagga gtttgtcaag atcctgcgct atgagaatga ggtgttgcag 240
ctggaggagg atgagcgctt cgagggccgc gtggtgtgga atggcagccg gggcaccaaa 300
gacctgcagg atctgtctat cttcatcacc aatgtcacct acaaccactc gggcgactac 360
gagtgccacg tctaccgcct gctcttcttc gaaaactacg agcacaacac cagcgtcgtc 420
aagaagatcc acattgaggt agtggacaaa ggtgagtcgg gtgctgcctg cccctttacc 480
gtcacccacc ggagagccag atggagggac agatggcagg cagtggacag gacaggctgg 540
ctctgtgcct ggccagccaa ccgcccacag cagcgggctg aggggaggg gagcagcccc 600
tcctgcccac tccagctctg gcctctgttt ctctccagcc cacggagagg tcaaagcatg 660
cctgtccccc acagacgctc cgggtacaga acccagctct gtcacctgtg ctgtatgacc 720
tctggcaggt gccttctgtc tctgagccaa agggttgtcc tgggcttgcc cggataata 780
atccgatgtg ttttctcggg gtgtggtttga gccattcttc catcatgggg ttcatgagga 840
ttgagcagct gcaggcacac cctggcttcc agcagagcct tgcaggtggt ggcgagggtg 900
gcggttctta ctgttgagta gctcagccct gctgctctct gtggtgatga ggcaagagag 960
cgtgcctgtg ttgg 974

<210> 14
<211> 268
<212> PRT
<213> Homo sapiens
<400> 14
Met Gly Arg Leu Leu Ala Leu Val Val Gly Ala Ala Leu aSle
r Ser 15 10 15
Ala Cys Gly Gly Cys Val Glu Val Asp Ser Glu Thr Glu Ala Val
Tyr
20 25 30
Gly Met Thr Phe Lys Ile Leu Cys Ile Ser Cys Lys Arg Arg Ser
Glu
35 40 45
Thr Asn Ala Glu Thr Phe Thr Glu Trp Thr Phe Arg Gln Lys
Gly Thr
50 55 60
Glu Glu Phe Val Lys Ile Leu Arg Tyr Glu Asn Glu Val Leu Gln
Leu
65 70 75 80
Glu Glu Asp Glu Arg Phe Glu Gly Arg Val Val Trp Asn Gly
Ser Arg
85 90 95
Gly Thr Lys Asp Leu Gln Asp Leu Ser Ile Phe Ile Thr Asn
Val Thr
100 105 110
Tyr Asn His Ser Gly Asp Tyr Glu Cys His Val Tyr Arg Leu Leu
Phe
115 120 125
Phe Glu Asn Tyr Glu His Asn Thr Ser Val Val Lys Lys Ile His
Ile
130 135 140
Glu Val Val Asp Lys Gly Glu Ser Gly Ala Ala Cys Pro Phe Thr
Val
145 150 155 160
Thr His Arg Arg Ala Arg Trp Arg Asp Arg Trp Gln Ala Val Asp
Arg
165 170 175
Thr Gly Trp Leu Cys Ala Trp Pro Ala Asn Arg Pro Gln Gln
Arg Ala
180 185 190
Glu Gly Glu Gly Ser Ser Pro Ser Cys Pro Leu Gln Leu Trp Pro
Leu
195 200 205
Phe Leu Ser Ser Pro Arg Arg Gly Gln Ser Met Pro Val Pro His
Arg
210 215 220
Arg Ser Gly Tyr Arg Thr Gln Leu Cys His Leu Cys Cys Met
Thr Ser
225 230 235 240
Gly Arg Cys Leu Leu Ser Leu Ser Gln Arg Val Val Leu Gly
Leu Pro
245 250 255
Gly Ile Ile Ile Arg Cys Val Ser Arg Gly Val Val
260 265

SEQUENCE LISTING

<160> NUMBER OF SEQ ID NOS: 17

<210> SEQ ID NO 1
<211> LENGTH: 27
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 1
ccatcctaat acgactcact atagggc                                            27

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tggaccttcc gccagaaggg cactg                                              25

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctggaggagg atgagcgctt cgag                                               24

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctattcggcc acctggacgc c                                                  21

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtgtctgaga tcatgatg                                                      18

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gccatgggga ggctgctggc cttagtggtc                                         30

<210> SEQ ID NO 7
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 7
gtgtgcctgc agctgctcaa                                                   20

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Trp Arg Asp Arg Trp Gln Ala Val Asp Arg Thr Gly Cys
 1               5                  10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Val Pro His Arg Arg Ser Gly Tyr Arg Thr Gln Leu
 1               5                  10

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcaaagcatg cctgtccc                                                     18

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcaaaccaca ccccgagaaa                                                   20

<210> SEQ ID NO 12
<211> LENGTH: 807
<212> TYPE: DNA
<213> ORGANISM: Homo sapiens

<400> SEQUENCE: 12
atggggaggc tgctggcctt agtggtcggc gcggcactgg tgtcctcagc ctgcgggggc        60
tgcgtggagg tggactcgga gaccgaggcc gtgtatggga tgaccttcaa aattctttgc       120
atctcctgca agcgccgcag cgagaccaac gctgagacct tcaccgagtg gaccttccgc       180
cagaagggca ctgaggagtt tgtcaagatc ctgcgctatg agaatgaggt gttgcagctg       240
gaggaggatg agcgcttcga gggccgcgtg gtgtggaatg caggcggg caccaaagac        300

-continued

```
ctgcaggatc tgtctatctt catcaccaat gtcacctaca accactcggg cgactacgag    360
tgccacgtct accgcctgct cttcttcgaa aactacgagc acaacaccag cgtcgtcaag    420
aagatccaca ttgaggtagt ggacaaaggt gagtcgggtg ctgcctgccc ctttaccgtc    480
acccaccgga gagccagatg gagggacaga tggcaggcag tggacaggac aggctggctc    540
tgtgcctggc cagccaaccg cccacagcag cgggctgagg gggaggggag cagcccctcc    600
tgcccactcc agctctggcc tctgtttctc tccagcccac ggagaggtca aagcatgcct    660
gtcccccaca gacgctccgg gtacagaacc cagctctgtc acctgtgctg tatgacctct    720
ggcaggtgcc ttctgtctct gagccaaagg gttgtcctgg gcttgcccgg gataataatc    780
cgatgtgttt ctcggggtgt ggtttga                                        807
```

<210> SEQ ID NO 13
<211> LENGTH: 974
<212> TYPE: DNA
<213> ORGANISM: Homo sapiens

<400> SEQUENCE: 13

```
gccatgggga ggctgctggc cttagtggtc ggcgcggcac tggtgtcctc agcctgcggg     60
ggctgcgtgg aggtggactc ggagaccgag gccgtgtatg ggatgacctt caaaattctt    120
tgcatctcct gcaagcgccg cagcgagacc aacgctgaga ccttcaccga gtggaccttc    180
cgccagaagg gcactgagga gtttgtcaag atcctgcgct atgagaatga ggtgttgcag    240
ctggaggagg atgagcgctt cgagggccgc gtggtgtgga atggcagccg ggcaccaaa    300 gacctgcagg atctgtctat cttcatcacc aatgtcacct acaaccactc gggcgactac    360
gagtgccacg tctaccgcct gctcttcttc gaaaactacg agcacaacac cagcgtcgtc    420
aagaagatcc acattgaggt agtggacaaa ggtgagtcgg gtgctgcctg cccctttacc    480
gtcacccacc ggagagccag atggagggac agatggcagg cagtggacag gacaggctgg    540
ctctgtgcct ggccagccaa cgcccacag cagcgggctg aggggaggg gagcagcccc    600 tcctgcccac tccagctctg gcctctgttt ctctccagcc cacggagagg tcaaagcatg    660
cctgtccccc acagacgctc cgggtacaga acccagctct gtcacctgtg ctgtatgacc    720
tctggcaggt gccttctgtc tctgagccaa agggttgtcc tgggcttgcc cgggataata    780
atccgatgtg tttctcgggg tgtggtttga gccattcttc atcatggggg ttcatgagga    840
ttgagcagct gcaggcacac cctggcttcc agcagagcct tgcaggtggt ggcgagggtg    900
gcggttctta ctgttgagta gctcagccct gctgctctct gtggtgatga ggcaagagag    960
cgtgcctgtg ttgg                                                      974
```

<210> SEQ ID NO 14
<211> LENGTH: 268
<212> TYPE: PRT
<213> ORGANISM: Homo sapiens

<400> SEQUENCE: 14

```
Met Gly Arg Leu Leu Ala Leu Val Val Gly Ala Ala Leu Val Ser Ser
 1               5                  10                  15

Ala Cys Gly Gly Cys Val Glu Val Asp Ser Glu Thr Glu Ala Val Tyr
            20                  25                  30

Gly Met Thr Phe Lys Ile Leu Cys Ile Ser Cys Lys Arg Arg Ser Glu
        35                  40                  45

Thr Asn Ala Glu Thr Phe Thr Glu Trp Thr Phe Arg Gln Lys Gly Thr
    50                  55                  60
```

```
Glu Glu Phe Val Lys Ile Leu Arg Tyr Glu Asn Glu Val Leu Gln Leu
 65                  70                  75                  80

Glu Glu Asp Glu Arg Phe Glu Gly Arg Val Val Trp Asn Gly Ser Arg
             85                  90                  95

Gly Thr Lys Asp Leu Gln Asp Leu Ser Ile Phe Ile Thr Asn Val Thr
            100                 105                 110

Tyr Asn His Ser Gly Asp Tyr Glu Cys His Val Tyr Arg Leu Leu Phe
            115                 120                 125

Phe Glu Asn Tyr Glu His Asn Thr Ser Val Val Lys Lys Ile His Ile
        130                 135                 140

Glu Val Val Asp Lys Gly Glu Ser Gly Ala Ala Cys Pro Phe Thr Val
145                 150                 155                 160

Thr His Arg Arg Ala Arg Trp Arg Asp Arg Trp Gln Ala Val Asp Arg
                165                 170                 175

Thr Gly Trp Leu Cys Ala Trp Pro Ala Asn Arg Pro Gln Gln Arg Ala
            180                 185                 190

Glu Gly Glu Gly Ser Ser Pro Ser Cys Pro Leu Gln Leu Trp Pro Leu
        195                 200                 205

Phe Leu Ser Ser Pro Arg Arg Gly Gln Ser Met Pro Val Pro His Arg
210                 215                 220

Arg Ser Gly Tyr Arg Thr Gln Leu Cys His Leu Cys Met Thr Ser
225                 230                 235                 240

Gly Arg Cys Leu Leu Ser Leu Ser Gln Arg Val Val Leu Gly Leu Pro
                245                 250                 255

Gly Ile Ile Ile Arg Cys Val Ser Arg Gly Val Val
            260                 265

<210> SEQ ID NO 15
<211> LENGTH: 273
<212> TYPE: PRT
<213> ORGANISM: Rattus norvegicus

<400> SEQUENCE: 15

Met Gly Thr Leu Leu Ala Leu Val Val Gly Ala Val Leu Val Ser Ser
  1               5                  10                  15

Ala Trp Gly Gly Cys Val Glu Val Asp Ser Glu Thr Glu Ala Val Tyr
             20                  25                  30

Gly Met Thr Phe Lys Ile Leu Cys Ile Ser Cys Lys Arg Arg Ser Glu
         35                  40                  45

Thr Thr Ala Glu Thr Phe Thr Glu Trp Thr Phe Arg Gln Lys Gly Thr
     50                  55                  60

Glu Glu Phe Val Lys Ile Leu Arg Tyr Glu Asn Glu Val Leu Gln Leu
 65                  70                  75                  80

Glu Glu Asp Glu Arg Phe Glu Gly Arg Val Val Trp Asn Gly Ser Arg
             85                  90                  95

Gly Thr Lys Asp Leu Gln Asp Leu Ser Ile Phe Ile Thr Asn Val Thr
            100                 105                 110

Tyr Asn His Ser Gly Asp Tyr Glu Cys His Val Tyr Arg Leu Leu Phe
            115                 120                 125

Phe Asp Asn Tyr Glu His Asn Thr Ser Val Val Lys Lys Ile His Leu
        130                 135                 140

Glu Val Val Asp Lys Gly Lys Trp Ser Leu Val Thr Leu Trp Gln Ala
145                 150                 155                 160

Arg Trp Arg Asp Arg Trp Lys Glu Gly Asp Arg Leu Val Ser His Arg
```

```
                165                 170                 175
Gly Gln Leu Thr Pro Arg Ser His Arg Gly Lys Asp Thr Pro Phe Leu
            180                 185                 190
Val Leu Glu Thr Ser Ala Leu Gln His Thr Gly Gly Gln Ile Arg Thr
        195                 200                 205
Pro Thr Pro Pro Thr Asn Gly Met Cys Ile Gly Leu His Ser Cys
    210                 215                 220
Cys Val Thr Ser Asp Gly Cys Ile Pro Ile Ser Glu Pro Gln Ala Cys
225                 230                 235                 240
Pro Gln Gly Pro Glu Arg Ile Phe Cys Met Ala Cys Cys Val Ser Gln
            245                 250                 255
Ala Gly Pro His Trp Arg Asp Val Gly Thr Tyr Leu Arg Pro Gln Trp
        260                 265                 270
Glu

<210> SEQ ID NO 16
<211> LENGTH: 249
<212> TYPE: PRT
<213> ORGANISM: Homo sapiens

<400> SEQUENCE: 16

Met Gly Arg Leu Leu Ala Leu Val Val Gly Ala Ala Leu Val Ser Ser
1               5                   10                  15
Ala Cys Gly Gly Cys Val Glu Val Asp Ser Glu Thr Glu Ala Val Tyr
            20                  25                  30
Gly Met Thr Phe Lys Ile Leu Cys Ile Ser Cys Lys Arg Arg Ser Glu
        35                  40                  45
Thr Asn Ala Glu Thr Phe Thr Glu Trp Thr Phe Arg Gln Lys Gly Thr
    50                  55                  60
Glu Glu Phe Val Lys Ile Leu Arg Tyr Glu Asn Glu Val Leu Gln Leu
65                  70                  75                  80
Glu Glu Asp Glu Arg Phe Glu Gly Arg Val Val Trp Asn Gly Ser Arg
                85                  90                  95
Gly Thr Lys Asp Leu Gln Asp Leu Ser Ile Phe Ile Thr Asn Val Thr
            100                 105                 110
Tyr Asn His Ser Gly Asp Tyr Glu Cys His Val Tyr Arg Leu Leu Phe
        115                 120                 125
Phe Glu Asn Tyr Glu His Asn Thr Ser Val Val Lys Lys Ile His Ile
    130                 135                 140
Glu Val Val Asp Lys Gly Glu Ser Gly Ala Ala Cys Pro Phe Thr Val
145                 150                 155                 160
Thr His Arg Arg Ala Arg Trp Arg Asp Arg Trp Gln Ala Val Asp Arg
                165                 170                 175
Thr Gly Trp Leu Cys Ala Trp Pro Ala Asn Arg Pro Gln Gln Arg Ala
            180                 185                 190
Glu Gly Glu Gly Ser Ser Pro Ser Cys Pro Leu Gln Leu Trp Pro Leu
        195                 200                 205
Phe Leu Ser Ser Pro Arg Arg Gly Gln Ser Met Pro Val Pro His Arg
    210                 215                 220
Arg Ser Gly Tyr Arg Thr Gln Leu Cys His Leu Cys Cys Met Thr Ser
225                 230                 235                 240
Gly Arg Cys Leu Leu Ser Leu Ser Gln
                245
```

```
<210> SEQ ID NO 17
<211> LENGTH: 218
<212> TYPE: PRT
<213> ORGANISM: Homo sapiens

<400> SEQUENCE: 17

Met Gly Arg Leu Leu Ala Leu Val Val Gly Ala Ala Leu Val Ser Ser
 1               5                  10                  15

Ala Cys Gly Gly Cys Val Glu Val Asp Ser Glu Thr Glu Ala Val Tyr
                20                  25                  30

Gly Met Thr Phe Lys Ile Leu Cys Ile Ser Cys Lys Arg Arg Ser Glu
             35                  40                  45

Thr Asn Ala Glu Thr Phe Thr Glu Trp Thr Phe Arg Gln Lys Gly Thr
 50                  55                  60

Glu Glu Phe Val Lys Ile Leu Arg Tyr Glu Asn Glu Val Leu Gln Leu
 65                  70                  75                  80

Glu Glu Asp Glu Arg Phe Glu Gly Arg Val Val Trp Asn Gly Ser Arg
                 85                  90                  95

Gly Thr Lys Asp Leu Gln Asp Leu Ser Ile Phe Ile Thr Asn Val Thr
                100                 105                 110

Tyr Asn His Ser Gly Asp Tyr Glu Cys His Val Tyr Arg Leu Leu Phe
            115                 120                 125

Phe Glu Asn Tyr Glu His Asn Thr Ser Val Val Lys Lys Ile His Ile
130                 135                 140

Glu Val Val Asp Lys Ala Asn Arg Asp Met Ala Ser Ile Val Ser Glu
145                 150                 155                 160

Ile Met Met Tyr Val Leu Ile Val Val Leu Thr Ile Trp Leu Val Ala
                165                 170                 175

Glu Met Ile Tyr Cys Tyr Lys Lys Ile Ala Ala Ala Thr Glu Thr Ala
                180                 185                 190

Ala Gln Glu Asn Ala Ser Glu Tyr Leu Ala Ile Thr Ser Glu Ser Lys
            195                 200                 205

Glu Asn Cys Thr Gly Val Gln Val Ala Glu
210                 215
```

What is claimed is:

1. An isolated protein encoded by a nucleic acid sequence having the sequence of SEQ ID NO: 12.

2. The protein according to claim 1, having an amino acid sequence of (SEQ.ID.NO.:14).

* * * * *